(12) United States Patent
Sato

(10) Patent No.: US 6,740,044 B2
(45) Date of Patent: May 25, 2004

(54) BLOOD-PRESSURE MONITORING APPARATUS FOR USE IN DIALYSIS, AND DIALYZING APPARATUS

(75) Inventor: Atsushi Sato, Komaki (JP)

(73) Assignee: Colin Corporation, Komaki (JP)

( * ) Notice: Subject to any disclaimer, the term of this patent is extended or adjusted under 35 U.S.C. 154(b) by 117 days.

(21) Appl. No.: 10/072,878

(22) Filed: Feb. 12, 2002

(65) Prior Publication Data

US 2002/0193691 A1 Dec. 19, 2002

(30) Foreign Application Priority Data

Jun. 13, 2001 (JP) ........................................ 2001-179274

(51) Int. Cl.⁷ ................................................. A61B 5/02
(52) U.S. Cl. ........................ 600/485; 600/481; 600/561
(58) Field of Search ................................. 600/481, 483, 600/485, 486, 490, 491, 492, 493, 494, 495, 496, 500, 561

(56) References Cited

U.S. PATENT DOCUMENTS

| | | |
|---|---|---|
| 4,718,891 A | 1/1988 | Lipps |
| 5,564,427 A | 10/1996 | Aso et al. |
| 5,752,920 A | 5/1998 | Ogura et al. |
| 5,876,348 A * | 3/1999 | Sugo et al. .................. 600/490 |

FOREIGN PATENT DOCUMENTS

| | | |
|---|---|---|
| EP | 0 311 709 A1 | 4/1989 |
| EP | 0 852 126 A2 | 7/1998 |
| JP | A 10-43147 | 2/1998 |

* cited by examiner

Primary Examiner—Max F. Hindenburg
Assistant Examiner—Navin Natnithithadha
(74) Attorney, Agent, or Firm—Oliff & Berridge, PLC

(57) ABSTRACT

A blood-pressure monitoring apparatus for use with a dialyzing device, including a blood-pressure-related-information obtaining device which iteratively obtains, from a patient who is undergoing a dialysis operation of the dialyzing device, a piece of blood-pressure-related information that can change in relation with a blood pressure of the patient, a change-value determining device, a memory device which stores, for the patient, a plurality of prescribed threshold values corresponding to a plurality of prescribed periods of an entire duration of the dialysis operation, and a judging device for judging that the blood pressure of the patient is abnormal.

10 Claims, 13 Drawing Sheets

BLOOD-PRESSURE MONITORING APPARATUS FOR USE IN DIALYSIS, AND DIALYZING APPARATUS

BACKGROUND OF THE INVENTION

1. Field of the Invention

The present invention relates to a blood-pressure monitoring apparatus for use in dialysis that continuously monitors change of blood pressure of a patient during a dialysis treatment, and to a dialyzing apparatus including the blood-pressure monitoring apparatus.

2. Related Art Statement

Since blood pressure of a patient who is undergoing a dialysis treatment may largely lower, there is a need to monitor the blood pressure. A blood-pressure measuring method using a cuff is preferable with respect to reliability. However, when the cuff is used to measure the blood pressure, it is needed to increase a pressure in the cuff up to a value higher than a systolic blood pressure of the patient. Thus, the patient feels discomfort, and accordingly blood-pressure measuring operations each using the cuff cannot be carried out so frequently.

Hence, there has been proposed a blood-pressure monitoring apparatus which successively obtains a piece of blood-pressure-related information that is related to blood pressure of a patient, successively determines an estimated blood pressure of the patient based each piece of blood-pressure-related information, and monitors, based on change of each estimated blood pressure, blood pressure of the patient who is undergoing a dialysis treatment. This blood-pressure monitoring apparatus is disclosed in, e.g., Japanese patent document No. 10-043147 or its corresponding U.S. Pat. No. 5,752,920. The monitoring apparatus iteratively determines an estimated blood pressure based on a pulse-wave propagation velocity at which a pulse wave propagates in patient's body. If change of the estimated blood pressure is greater than a prescribed threshold value, indicating that patient's blood pressure may be abnormal, then the monitoring apparatus carries out a blood-pressure measuring operation using a cuff to obtain a more reliable blood-pressure value of the patient.

During a dialysis treatment, blood pressure of a patient that is clinically normal may lower little by little as time elapses. Therefore, it is a conventional practice that when the above-indicated blood-pressure monitoring apparatus is used to monitor blood pressure of a patient during a dialysis treatment, a considerably great threshold value is employed in judging whether change of each estimated blood-pressure value is abnormal, so that a normal time-wise blood-pressure decrease may not be judged as abnormal. However, if the threshold value is too great, the monitoring apparatus cannot quickly find an abnormal blood-pressure decrease.

Thus, it is desirable that the above-indicated threshold value be as small as possible so long as the threshold value does not allow a normal blood-pressure decrease to be judged as abnormal. However, a normal amount of decreasing of blood pressure during a dialysis treatment depends on each individual patient, and an abnormal blood-pressure decreasing amount that needs an emergency treatment also depends on each patient. Thus, the conventional blood-pressure monitoring apparatus has the problems that a normal blood-pressure decrease for a patient may be judged as abnormal and that an abnormal blood-pressure decrease for another patient may not be quickly found. If the abnormal blood-pressure decrease is not quickly found, then the patient may loose his or her life. Therefore, there is a tendency that the threshold value is set at a considerably small value. Thus, normal blood-pressure decreases for a patient may be frequently judged as abnormal, and blood-pressure measuring operations each using a cuff may be carried out on the patient. That is, the patient may be forced to feel unnecessary discomfort.

Meanwhile, a conventional dialyzing apparatus is used such that when the blood-pressure monitoring apparatus generates an alarm sound indicative of the abnormal blood-pressure decrease, a doctor or a nurse hurries to lower a speed of operation of the dialyzing apparatus or temporarily stop the operation of the same. Thus, a considerably long time is taken to conduct an appropriate action to treat the abnormal blood-pressure decrease.

SUMMARY OF THE INVENTION

It is therefore an object of the present invention to provide a blood-pressure monitoring apparatus for use in dialysis that can quickly find an abnormal decrease of blood pressure of a patient without erroneously judging a normal blood-pressure decrease as being abnormal, and provide a dialyzing apparatus which can enable, when the abnormal blood-pressure decrease is found, the blood pressure of the patient to be quickly recovered.

The Inventor has carried out extensive studies to achieve the above-indicated objects, and found the facts that although a pattern of change of blood pressure during a dialysis treatment depends on each individual patient, blood pressure of each patient follows a substantially same pattern during each dialysis treatment and that the blood pressure of each patient tends to abnormally lower during only a particular period or periods within an entire duration of each dialysis treatment. Therefore, if a tight threshold value is used to find a blood-pressure abnormality during the particular period of each dialysis treatment, an abnormal blood-pressure decrease can be quickly found and, if a loose threshold value is used to find an abnormality during the remaining periods of each dialysis treatment, a normal blood-pressure decrease is not erroneously judged as abnormal.

As described above, blood pressure of each patient follows a substantially same pattern of change during each dialysis treatment. Therefore, if a time-wise change of blood-pressure values of each patient during each dialysis treatment is stored in a memory device and the blood-pressure values (or the change of the blood-pressure values) stored in the memory device are compared with actual blood-pressure values (or change of the actual blood-pressure values) obtained during each dialysis treatment, only an abnormal blood-pressure change can be monitored during each dialysis treatment and accordingly an abnormal blood-pressure decrease can be quickly found without erroneously judging a normal blood-pressure change as abnormal. The present inventions have been developed based on these findings.

The above objects have been achieved by the present invention. According to a first feature of the present invention, there is provided a blood-pressure monitoring apparatus for use with a dialyzing device, comprising a blood-pressure-related-information obtaining device which iteratively obtains, from a patient who is undergoing a dialysis operation of the dialyzing device, a piece of blood-pressure-related information that can change in relation with a blood pressure of the patient; a change-value determining means for determining a change value representing a change of each piece of blood-pressure-related information iteratively obtained by the blood-pressure-related-information obtaining device; a memory device which stores, for the patient, a plurality of prescribed threshold values corresponding to a plurality of prescribed periods of an entire duration of the dialysis operation, wherein at least one of the threshold values that corresponds to at least one of the prescribed periods is smaller than the other threshold values, and wherein the blood pressure of the patient is more likely to lower during the at least one period of the entire duration, than during the other periods of the entire duration; and a judging means for judging that the blood pressure of the patient is abnormal, when the change value determined by the change-value determining means is greater than one of the threshold values that corresponds to one of the prescribed periods that includes a dialysis time, measured from a commencement of the dialysis operation, when the each piece of blood-pressure-related information is obtained by the blood-pressure-related-information obtaining device.

According to this invention, the change-value determining means determines a change value representing a change of each piece of blood-pressure-related information iteratively obtained by the blood-pressure-related-information obtaining device, and the judging means may find a blood-pressure abnormality, even if a smaller change value may be determined during a period of the entire duration in which the blood pressure of the patient is more likely to lower, than a change value determined during the other periods of the entire duration. In other words, during a period in which the blood pressure is less likely to lower, a greater change value may not be judged as abnormal, than a change value determined during a period in which the blood pressure is more likely to lower. Thus, an abnormal blood-pressure decrease can be quickly found without erroneously judging a normal blood-pressure decrease as abnormal.

According to a second feature of the present invention, there is provided a blood-pressure monitoring apparatus for use with a dialyzing device, comprising a blood-pressure-related-information obtaining device which iteratively obtains, from a patient who is undergoing a dialysis operation of the dialyzing device, a piece of blood-pressure-related information that can change in relation with a blood pressure of the patient; a memory device which stores a normal relationship between blood-pressure-related information and dialysis time; and a judging means for judging that the blood pressure of the patient is abnormal, when a comparison value is greater than a prescribed threshold value, the comparison value being obtained from each piece of blood-pressure-related information iteratively obtained by the blood-pressure-related-information obtaining device, with a piece of blood-pressure-related information, represented by the normal relationship stored in the memory device, that corresponds to a dialysis time, measured from a commencement of the dialysis operation, when the each piece of blood-pressure-related information is obtained by the blood-pressure-related-information obtaining device.

According to this invention, the memory device may store a normal relationship between blood-pressure-related information and dialysis time that is particularly appropriate for each individual patient. This normal relationship represents a normal change of blood pressure of the patient during each dialysis treatment. The judging means obtains a comparison value from each piece of blood-pressure-related information iteratively obtained by the blood-pressure-related-information obtaining device, and a piece of blood-pressure-related information, represented by the normal relationship stored in the memory device, that corresponds to a dialysis time when the each piece of blood-pressure-related information is obtained, and finds a blood-pressure abnormality of the patient based on the thus obtained comparison value. Thus, the present apparatus finds a blood-pressure abnormality based on only an abnormal blood-pressure change, and accordingly can quickly find an abnormal blood-pressure decrease without erroneously judging a normal blood-pressure decrease as abnormal.

According to a third feature of the present invention that includes the second feature (2), the judging means comprises a comparison-value determining means for determining the comparison value by comparing the each piece of blood-pressure-related information obtained by the blood-pressure-related-information obtaining device, with the piece of blood-pressure-related information, represented by the normal relationship stored in the memory device, that corresponds to the dialysis time when the each piece of blood-pressure-related information is obtained by the blood-pressure-related-information obtaining device.

According to this invention, the judging means finds a blood-pressure abnormality when the comparison value determined by the comparison-value determining means is greater than the prescribed threshold value. The comparison value may represent a difference between a piece of blood-pressure-related information, represented by the normal relationship stored in the memory device for the patient, that corresponds to a dialysis time, and a piece of blood-pressure-related information actually obtained from the patient by the blood-pressure-related-information obtaining device at the dialysis time. This means that the judging means finds a blood-pressure abnormality by comparing the normal relationship for the patient and the piece of blood-pressure-related information actually obtained from the patient, with each other. Thus, the present apparatus finds a blood-pressure abnormality based on only an abnormal blood-pressure change, and accordingly can quickly find an abnormal blood-pressure decrease without erroneously judging a normal blood-pressure decrease as abnormal.

According to a fourth feature of the present invention that includes the second feature (2), the monitoring apparatus further comprises a correcting means for correcting an entirety of the normal relationship stored in the memory device, to a corrected normal relationship, such that a piece of blood-pressure-related information obtained by the blood-pressure-related-information obtaining device at a time of commencement of the dialysis operation is equal to a corrected piece of blood-pressure-related information, represented by the corrected normal relationship, that corresponds to the time of commencement of the dialysis operation, wherein the judging means comprises a comparison-value determining means for determining a comparison value by comparing a piece of blood-pressure-related information obtained by the blood-pressure-related-information obtaining device at a dialysis time measured from the time of commencement of the dialysis operation, with a corrected piece of blood-pressure-related information, represented by the corrected normal relationship, that corresponds to the dialysis time.

Blood pressure of each patient will change in day even if the patient would be healthy. The comparison value determined by the comparison-value determining means in accordance with the third feature (3) does not exclude the normal change of blood pressure of the patient. In contrast, according to the fourth feature (4), the correcting means corrects an entirety of the normal relationship stored for the patient in the memory device, to a corrected normal relationship, such that the piece of blood-pressure-related information actually obtained from the patient by the blood-pressure-related-information obtaining device at the time of commencement of the dialysis operation is equal to the corrected piece of blood-pressure-related information, represented by the corrected normal relationship, that corresponds to the time of commencement of the dialysis operation. This corrected normal relationship does not include the normal change of blood pressure of the patient. The comparison-value determining means determines a comparison value by comparing a piece of blood-pressure-related information obtained by the blood-pressure-related-information obtaining device at a dialysis time, with a corrected piece of blood-pressure-related information, represented by the corrected normal relationship, that corresponds to the dialysis time, and the judging means finds a blood-pressure abnormality based on the thus determined comparison value. Thus, the present apparatus can more quickly find an abnormal blood-pressure decrease without erroneously judging a normal blood-pressure decrease as abnormal.

According to a fifth feature of the present invention, the monitoring apparatus further comprises an actual-change-value determining means for determining an actual change value of each piece of blood-pressure-related information iteratively obtained by the blood-pressure-related-information obtaining device; and a normal-change-value determining means for determining a normal change value by which the blood-pressure-related information, represented by the normal relationship stored in the memory device, changes in a period in which the each piece of blood-pressure-related information has changed by the actual change value determined by the actual-change-value determining means, wherein the judging means obtains the comparison value by comparing the actual change value determined by the actual-change-value determining means, with the normal change value determined by the normal-change-value determining means.

According to this invention, the judging means may find a blood-pressure abnormality, e.g., when a difference between the actual change value and the normal change value is greater than the prescribed threshold value. The actual change value represents an actual change of blood pressure of the patient during the dialysis treatment; and the normal change value represents a normal change of blood pressure of the patient during each dialysis treatment. Therefore, the judging means finds a blood-pressure abnormality by comparing the actual blood-pressure change during the dialysis treatment with the normal blood-pressure change during each dialysis treatment. Thus, the present apparatus finds a blood-pressure abnormality based on only an abnormal blood-pressure change, and accordingly can quickly find an abnormal blood-pressure decrease without erroneously judging a normal blood-pressure decrease as abnormal.

According to a sixth feature of the present invention, the memory device stores, as the normal relationship, an average of a plurality of normal relationships, each between blood-pressure-related information and dialysis time, that have been obtained by the blood-pressure-related-information obtaining device during a plurality of dialysis operations which have been carried out on the patient, and the monitoring apparatus further comprises an updating means for updating the normal relationship stored in the memory device, based on a relationship between blood-pressure-related information and dialysis time that is obtained by the blood-pressure-related-information obtaining device during the dialysis operation, when the judging means does not judge, during the dialysis operation, that the blood pressure of the patient is abnormal.

According to this invention, the updating means updates the normal relationship stored in the memory device, based on a relationship between blood-pressure-related information and dialysis time that is obtained during the current dialysis operation. Thus, the present apparatus can update the normal relationship although the blood pressure of the patient naturally increases as the age of the patient increases. Therefore, the present apparatus can quickly find an abnormal blood-pressure decrease without erroneously judging a normal blood-pressure decrease as abnormal.

According to a seventh feature of the present invention, there is provided a dialyzing apparatus, comprising a dialyzer; a pump which controls an amount of a dialyzing fluid that is supplied to the dialyzer; a blood-pressure monitoring apparatus according to any of the first to sixth features (1) to (6); and a fluid-amount control means for controlling, when the judging means judges that the blood pressure of the patient is abnormal, the pump to decrease the amount of the dialyzing fluid supplied to the dialyzer.

According to this invention, when the judging means finds a blood-pressure abnormality, the fluid-amount control means automatically controls the pump to decrease the amount of the dialyzing fluid supplied to the dialyzer. Thus, the present apparatus can quickly cause the blood pressure of the patient to be recovered.

BRIEF DESCRIPTION OF THE DRAWINGS

The above and optional objects, features, and advantages of the present invention will be better understood by reading the following detailed description of preferred embodiments of the invention when considered in conjunction with the accompanying drawings, in which.

DETAILED DESCRIPTION OF PREFERRED EMBODIMENTS

Figure 1:
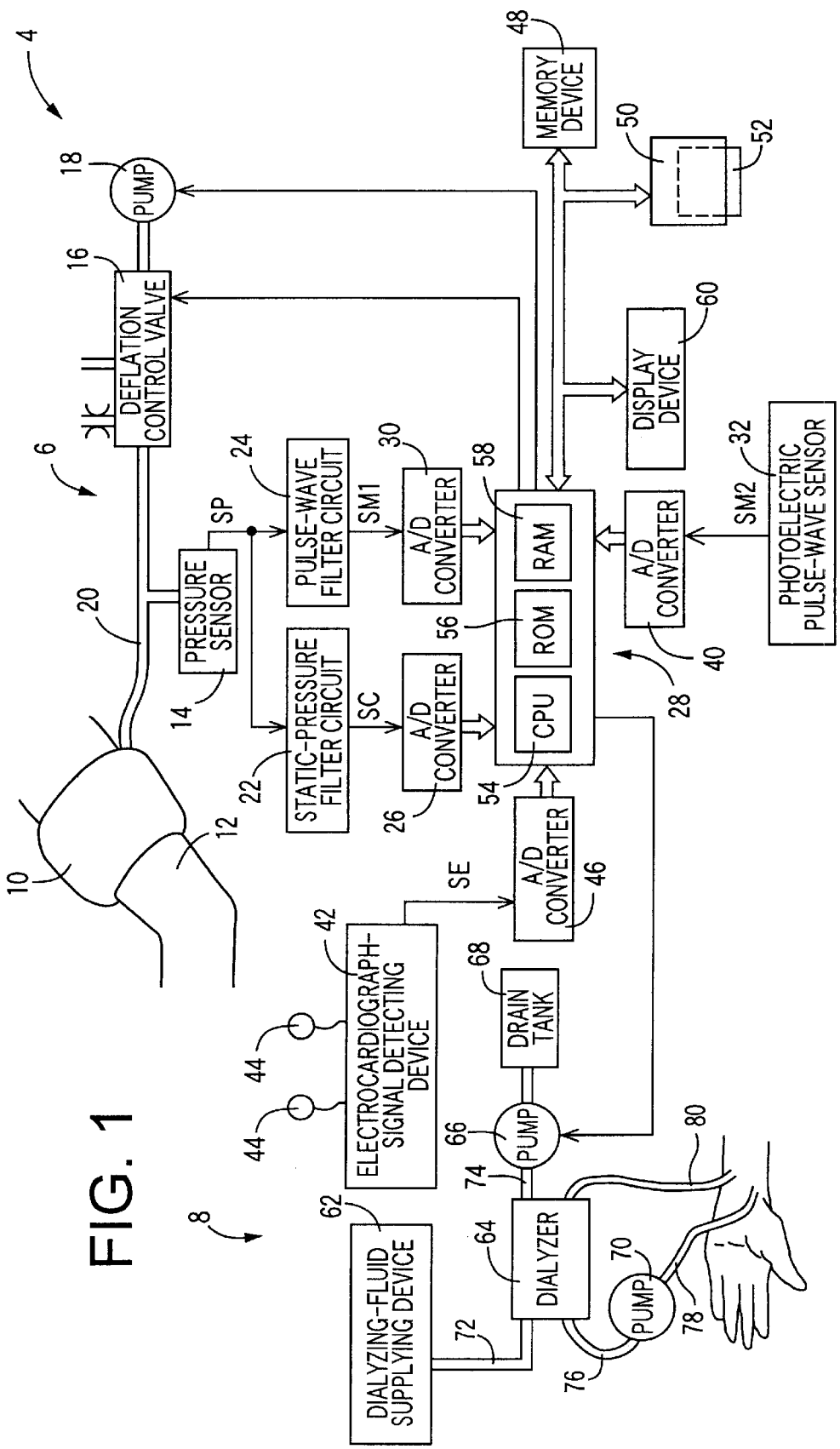
FIG. 1 is a diagrammatic view for explaining a construction of a dialyzing apparatus to which the present invention is applied.

Hereinafter, there will be described an embodiment of the present invention, by reference to the drawings. FIG. 1 is a diagrammatic view for explaining a construction of a dialyzing apparatus 4 to which the present invention is applied. The dialyzing apparatus 4 includes a blood-pressure monitor section 6 and a blood dialysis section 8. First, the blood-pressure monitor section 6 will be described below.

In FIG. 1, reference numeral 10 designate a cuff which includes a belt-like cloth bag and a rubber bag accommodated in the cloth bag and which is wound around, e.g., an upper portion 12 of one arm of a patient that is not connected to a dialyzer 64, described later. The cuff 10 is connected to a pressure sensor 14, a deflation control valve 16, and an air pump 18 via a piping 20. The deflation control valve 16 is selectively placed in a pressure-supply position in which the control valve 16 permits a pressurized air to be supplied from the air pump 18 to the cuff 10, a slow-deflation position in which the control valve 16 permits the pressurized air to be slowly discharged from the cuff 10, and a quick-deflation position in which the control valve 16 permits the pressurized air to be quickly discharged from the cuff 1D.

The pressure sensor 14 detects an air pressure PK in the cuff 10, and supplies a pressure signal SP representing the detected pressure PK, to each of a static-pressure filter circuit 22 and a pulse-wave filter circuit 24. The static-pressure filter circuit 22 includes a low-pass filter and extracts, from the pressure signal SP, a static-pressure component contained in the pressure signal SP, i.e., a cuff pressure signal SC representing the static or pressing pressure in the cuff 10. The cuff pressure signal SC is supplied to a control device 28 via an A/D (analog-to-digital) converter 26. The pulse-wave filter circuit 24 includes a band-pass filter and extracts, from the pressure signal SP, an oscillating component having predetermined frequencies, i.e., a cuff-pulse-wave signal SM1. The cuff-pulse-wave signal SM1 is supplied to the control device 28 via an A/D converter 30. The cuff-pulse-wave signal SM1 represents a cuff pulse wave which is produced from a brachial artery of the upper arm 12 in synchronism with heartbeat of the patient and is propagated to the cuff 10.

Figure 2:
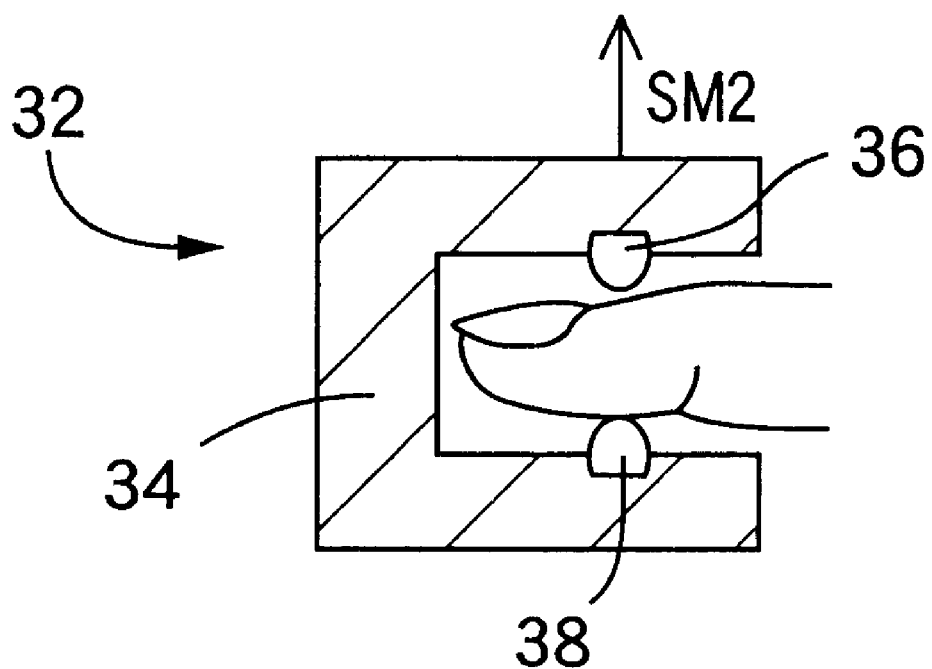
FIG. 2 is a cross-sectional view showing a construction of a photoelectric pulse-wave sensor of the apparatus of FIG. 1.

A photoelectric pulse-wave sensor 32 functions as a volumetric-pulse-wave detecting device. The sensor 32 detects a volumetric pulse wave (i.e., a plethysmograph) representing a volume of blood present in peripheral blood vessels of a living subject. The sensor 32 is worn on, e.g., an end portion of a finger of the other arm than the arm around which the cuff 10 is wound. The photoelectric pulse-wave sensor 32 has the same construction as that of a known sensor used to detect pulse rate. As shown in detail in FIG. 2, the sensor 32 includes a housing 34 that can accommodate a portion of a living subject, such as an end portion of a finger; a light emitting element 36 as a light source that is disposed on one of opposite walls of the housing 34 and emits, toward skin of the subject, a red or infrared light in a wavelength range that can be reflected by hemoglobin, preferably a light having a wavelength of, e.g., about 800 nm, that is not influenced by blood oxygen saturation; and a light receiving element 38 that is disposed on the other wall of the housing 34 such that the light receiving element 38 is opposed to the light emitting element 36, and detects the light transmitted through the portion of the subject. The light receiving element 38 produces a photoelectric-pulse-wave signal SM2 representing the detected amount of light, i.e., volume of blood present in capillaries of the portion of the subject, and supplies the photoelectric-pulse-wave signal SM2 to the control device 28 via an AID converter 40.

An electrocardiograph (ECG) signal detecting device 42 continuously detects an ECG wave WH, i.e., so-called electrocardiogram (ECG) representing an action potential of cardiac muscle of the subject, through a plurality of electrodes 44 which are adhered to respective prescribed locations of the subject, and supplies an ECG signal SE representing the detected ECG wave WH, to the control device 28 via an A/D converter 56.

A memory device 48 is provided by a well known memory means such as a RAM (random access memory), a magnetic-disc device (HDD), or a removable media (MO, DVD, etc.). The memory device 48 stores, for individual patients, respective arrays of abnormality-judgment thresholds, and respective normal relationships between blood-pressure-related information and dialysis time. An identification-code reading device 50 reads an identification (ID) code of a patient that is recorded on a magnetic card 52 inserted in the reading device 50, and supplies a signal representing the read ID code., to the control device 28.

The control device 28 is provided by a so-called microcomputer including a CPU (central processing unit) 54, a ROM (read only memory) 56, a RAM 58, and an I/O port, not shown. The CPU 54 processes signals according to the control programs pre-stored in the ROM 56 by utilizing the temporary-storage function of the RAM 58, and controls the deflation control valve 16 and the air pump 18. In addition, the CPU 54 operates for identifying a patient, determining a blood-pressure value BP of the patient, successively determining estimated blood-pressure values EBP of the patient, finding or judging an abnormality of the blood pressure of the patient during a blood dialysis operation, and controlling what is displayed by a display device 60. Moreover, the CPU 54 controls respective rotation speeds of a negative-pressure pump 66 and a blood-circulation pump 70 of the blood dialysis section 8 that will be described later.

The blood dialysis section 8 has a construction similar to that of a common dialyzing device, and includes a dialyzing-fluid supplying device 62, the dialyzer 64, the negative-pressure pump 66, and the blood-circulation pump 70. The dialyzing-fluid supplying device 62 has the function of preparing a dialyzing fluid by mixing a concentrated fluid with water at a prescribed ratio, and includes a temperature controller for keeping the prepared dialyzing fluid at a prescribed temperature. The supplying device 62 is connected to the dialyzer 64 via a piping 72, and the dialyzer 64 is connected to the negative-pressure pump 66 via a piping 74. The negative-pressure pump 66 applies a negative pressure to respective inner spaces of the piping 72 and the piping 74 provided between the pump 66 and the supplying device 62, thereby introducing the dialyzing fluid accumulating in the supplying device 62, into the dialyzer 64.

The dialyzer 64 is connected to a radial artery, not shown, of the patient via a piping 76, the blood-circulation pump 70, and a piping 78. The circulation pump 70 introduces the blood from the radial artery to the dialyzer 64. The dialyzer 64 removes, owing to dialysis effect, etc., waste products and water from the blood of the patient into the dialyzing fluid, and introduces necessary ions from the dialyzing fluid into the blood. The blood cleaned by the dialyzer 64 is returned to an antebrachial vein, not shown, of the patient via a piping 80. Meanwhile, the dialyzing fluid containing the waste products received from the blood in the dialyzer 64 is sent, by the negative-pressure pump 66, to a drain tank 68.

Figure 3:
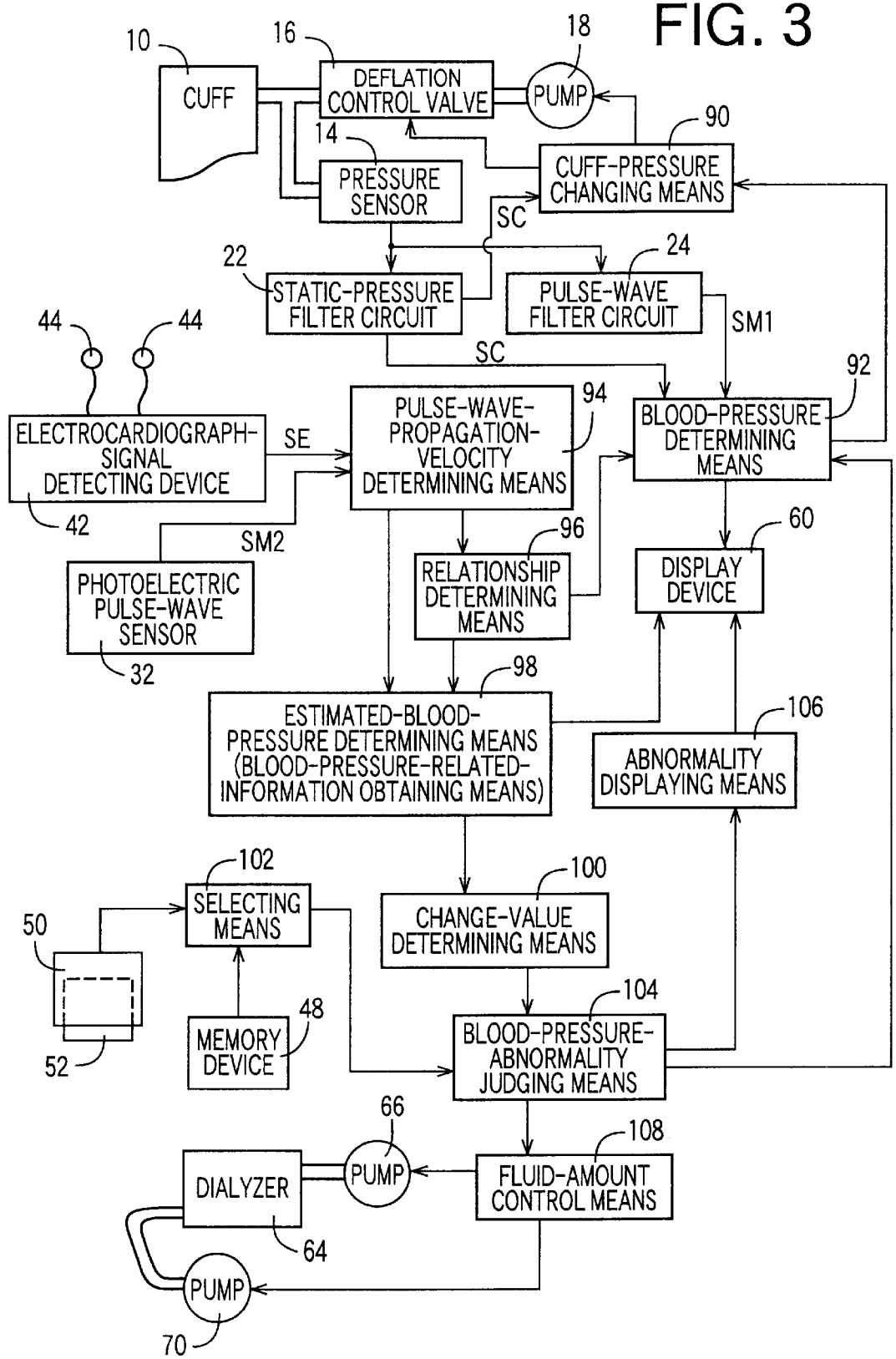
FIG. 3 is a block diagram for explaining essential control functions of a control device 28 of the apparatus of FIG. 1.

FIG. 3 is a block diagram for explaining essential functions of the control device 28. A cuff-pressure changing means 90 and a blood-pressure determining means 92 are operated each time a prescribed blood-pressure-measurement period TB, e.g., one hour, passes, or when a blood-pressure-abnormality judging means 104 finds or judges an abnormal change of blood pressure of the patient.

The cuff-pressure changing means 90 operates, based on the cuff pressure signal SC supplied from the static-pressure filter circuit 22, the air pump 18 and the deflation control valve 16 to quickly increase the pressing pressure of the cuff 10, i.e., the cuff pressure PC up to a prescribed target pressure (e.g., 180 mmHg) which would be higher than a systolic blood-pressure value $BP_{SYS}$ of the patient and subsequently slowly decrease the cuff pressure PC at a rate of from 2 to 3 mmHg/sec. After the blood-pressure determining means 92, described below, has determined a blood-pressure value BP of the patient, the cuff-pressure changing means 90 quickly decreases the cuff pressure PC down to atmospheric pressure.

The blood-pressure determining means 92 determines a systolic, a mean, and a diastolic blood-pressure value $BP_{SYS}$, $BP_{MEAN}$, $BP_{DIA}$ of the upper arm 12 of the patient, according to well-known oscillometric method, based on the cuff-pressure signal SC continuously supplied from the static-pressure filter circuit 22, and the cuff-pulse-wave signal SM1 continuously supplied from the pulse-wave filter circuit 24, each during the slow decreasing of the cuff pressure PC under the control of the cuff-pressure changing means 90. In addition, the blood-pressure determining means 92 operates the display device 60 to display the thus determined blood-pressure values $BP_{SYS}$, etc.

Figure 4:
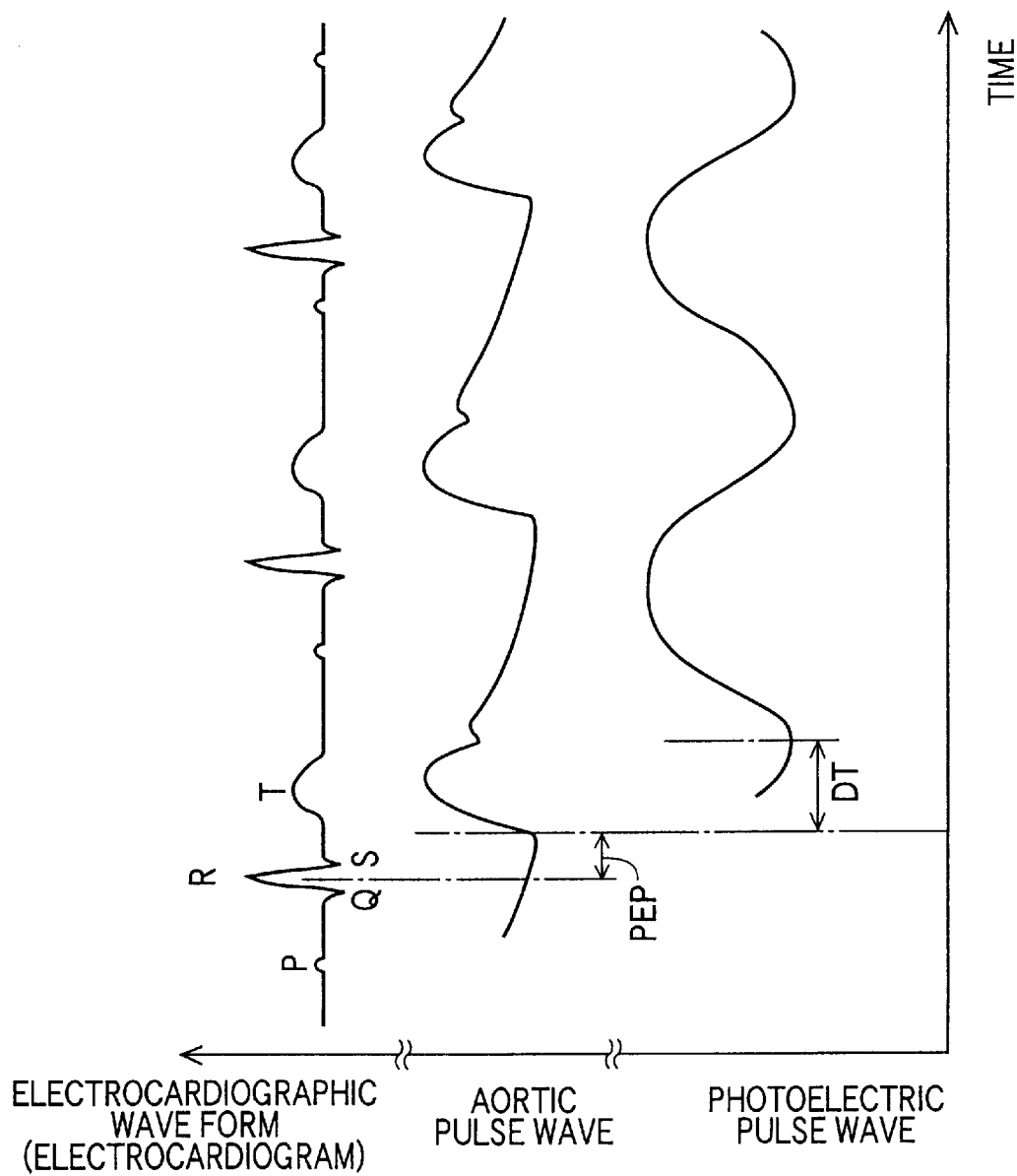
FIG. 4 is a graph for explaining a manner in which a pulse-wave propagation time DT is determined by a pulse-wave-propagation-velocity determining means 94 shown in FIG. 3.

A pulse-wave-propagation-velocity determining means 94 successively determines, as illustrated in FIG. 4, a time difference DT (i.e., a pulse-wave propagation time) between a periodic point (e.g., an R-wave) on each of successive heartbeat-synchronous pulses of the ECG wave continuously detected by the ECG-signal detecting device 42, and a periodic point (e.g., a rising or minimal point) on a corresponding one of successive heartbeat-synchronous pulses of the photoelectric pulse wave continuously detected by the photoelectric pulse-wave sensor 32. The determining means 94 successively determines, based on each of the pulse-wave propagation times DT successively determined for the successive heartbeat-synchronous pulses, a pulse-wave-propagation velocity PWV (m/sec) at which a pulse wave propagates through an artery of the patient, according to the following expression (1) pre-stored in the ROM 56:

$$PWV = L/(DT - PEP) \quad \text{(Expression 1)}$$

where L (m) is a distance from the left ventricle of the heart, via the aorta, to a position where the sensor 32 is worn on the patient, and is replaced with a constant value that is experimentally obtained in advance, and PEP (sec) is a pre-ejection period between an R-wave of the ECG wave and a rising point of an aortic pulse wave, and is replaced with a constant value that is experimentally obtained in advance.

A relationship determining means 96 determines coefficients α, β of the following expression (2) representing a relationship between estimated blood pressure EBP and pulse-wave-propagation velocity PWV, based on one of systolic, mean, and diastolic blood-pressure values $BP_{SYS}$, $BP_{MEAN}$, $BP_{DIA}$ determined by the blood-pressure determining means 92 in a blood-pressure measuring operation, and the pulse-wave-propagation velocity PWV determined by the pulse-wave-propagation-velocity determining means 94 during the blood-pressure measuring operation, or immediately before or after the measuring operation. For example, the coefficients α, β of the expression (2) are determined based on a first pair of a systolic blood pressure $BP_{SYS}$ determined by the blood-pressure determining means 92 in the current blood-pressure measuring operation and a pulse-wave propagation velocity PWV determined during the current measuring operation, and a second pair of a systolic blood pressure $BP_{SYS}$ determined by the means 92 in the last blood-pressure measuring operation and a pulse-wave propagation velocity PWV determined during the last measuring operation.

$$EBP = \alpha(PWV) + \beta \quad \text{(Expression 2)}$$

where α and β are positive constants.

If the systolic blood-pressure values $BP_{SYS}$ determined by the blood-pressure determining means 92 are used to determine the coefficients of the above-indicated expression (2), the expression (2) provides estimated systolic blood-pressure values $EBP_{SYS}$; if the mean blood-pressure values $BP_{MEAN}$ determined by the means 92 are used to determine the coefficients of the expression (2), the expression (2) provides estimated mean blood-pressure values $EBP_{MEAN}$; and if the diastolic blood-pressure values $BP_{DIA}$ determined by the means 92 are used to determine the coefficients of the expression (2), the expression (2) provides estimated diastolic blood-pressure values $EBP_{DIA}$. Which sort of blood-pressure values out of the systolic, mean, and diastolic blood-pressure values $BP_{SYS}$, $BP_{MEAN}$, $BP_{DIA}$ determined by the means 92 are selected to determine the expression (2) depends upon which sort of blood-pressure values out of systolic, mean, and diastolic blood-pressure values are continuously monitored as estimated blood-pressure values EBP.

An estimated-blood-pressure determining means 98 functioning as a blood-pressure-related-information obtaining means, successively and non-invasively determines, according to the expression (2) whose coefficients α, β have been determined by the relationship determining means 96, an estimated blood-pressure value EBP of the patient based on each of the pulse-wave-propagation velocities PWV successively determined by the wave-propagation-velocity determining means 94. In addition, the determining means 98 operates the display device 60 to display a time-wise change of the successively determined, estimated blood-pressure values EBP. Preferably, a period at which the determining means 98 determines an estimated blood-pressure value EBP is as short as the period of one heartbeat or several heartbeats, but it may be considerably long if it is shorter than the blood-pressure-measurement period TB of the blood-pressure determining means 92.

A change-value determining means 100 successively determines a change value of each of the estimated blood-pressure values EBP successively determined by the estimated-blood-pressure determining means 98. An estimated-blood-pressure change value means a rate of change, or an amount of change, of each of the successively determined, estimated blood-pressure values EBP from a reference estimated blood-pressure value EBP. The reference estimated blood-pressure value EBP may be an estimated blood-pressure value EBP determined when the current relationship (i.e., the current coefficients of the expression (2)) is determined by the relationship determining means 96, that is, the blood-pressure value BP determined by the blood-pressure determining means 92.

A selecting means 102 identifies, based on the ID code read by the ID-code reading device 50, the patient who will undergo a dialysis operation, and selects an array of abnormality-judgment threshold values for the identified patient, from the respective arrays of abnormality-judgment threshold values that are pre-stored in the memory device 48 for the individual patients. An array of abnormality-judgment threshold values are determined, in advance, such that a dialysis duration in which the dialysis operation lasts is divided into a plurality of time periods and those threshold values are assigned for the divided time periods, respectively. Since each individual patient has, in the dialysis duration, a specific time period in which his or her blood pressure lowers, a smaller threshold value than the other threshold values is assigned to the time period including the specific time.

Figure 5:
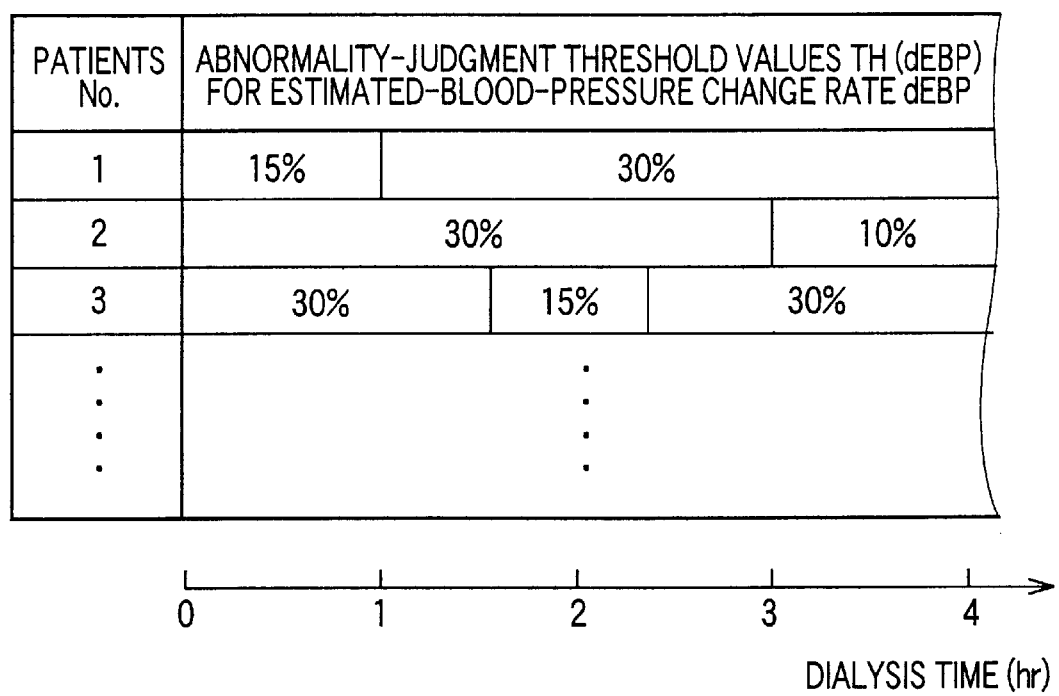
FIG. 5 is a schematic view showing arrays of abnormality-judgment threshold values which are stored, for individual patients, in a memory device 48 shown in FIG. 3, in the case where estimated-blood-pressure change rate dEBP is employed as estimated-blood-pressure change value.

FIG. 5 is a schematic view showing the arrays of abnormality-judgment threshold values which are stored, for the individual patients, in the memory device 48, in the case where estimated-blood-pressure change rate dEBP is employed as estimated-blood-pressure change value. For example, a patient having an ID code of "No. 1" has been known as a person whose blood pressure is highly likely to lower during an initial portion of an entire time duration of each dialysis operation. Therefore, an abnormality-judgment threshold value TH (dEBP) of 15% is assigned to the initial one-hour portion of the entire time duration, and a greater threshold value of 30% is assigned to the remaining portion of the entire time duration. A patient "No. 2" has been known as a person whose blood pressure is highly likely to lower during a terminal portion of the entire time duration of each dialysis operation. Therefore, a smaller abnormality-judgment threshold value TH (dEBP) is assigned to an after-three-hour portion of the entire time duration, than a threshold value assigned to an initial three-hour portion. In addition, since the patient "No. 2" has been known as a person who feels discomfort from a considerably small blood-pressure change, the threshold value TH(dEBP) assigned to the terminal after-three-hour portion for the patient "No. 2" is still smaller than that assigned to the initial one-hour portion for the patient "No. 1". For a patient "No. 3", a smaller abnormality-judgment threshold value TH(dEBP) is assigned to an intermediate portion of the entire time duration, than respective threshold values assigned to initial and terminal portions of the entire time duration. Generally speaking, each dialysis operation is started at a fixed time, and accordingly the intermediate portion of the entire time duration of each dialysis operation corresponds to a lunch time. Though not shown in FIG. 5, there are patients who have a plurality of time periods or portions in which their blood pressure is highly likely to lower.

A blood-pressure-abnormality judging means 104 judges that a lowering of the blood pressure of the patient is abnormal, when the estimated-blood-pressure change value determined by the change-value determining means 100 is greater than one of the abnormality-judgment threshold values, selected for the patient by the selecting means 102, that corresponds to a time duration which has elapsed from a commencement of each dialysis operation. When the judging means 104 judges that the blood pressure of the patient is abnormal, the judging means 104 operates the blood-pressure determining means 92 to measure, using the cuff 10, reliable blood-pressure values BP of the patient.

An abnormality displaying means 106 operates, when the blood-pressure-abnormality judging means 104 judges that the blood pressure of the patient is abnormal, the display device 60 to display the fact. A fluid-amount control means 108 lowers, when the blood-pressure-abnormality judging means 104 judges that the blood pressure of the patient is abnormal, the respective rotation speeds of the negative-pressure pump 66 and the blood-circulation pump 70, to respective prescribed lower rotation speed, or stops the respective rotation of the pumps 66, 70.

Figure 6:
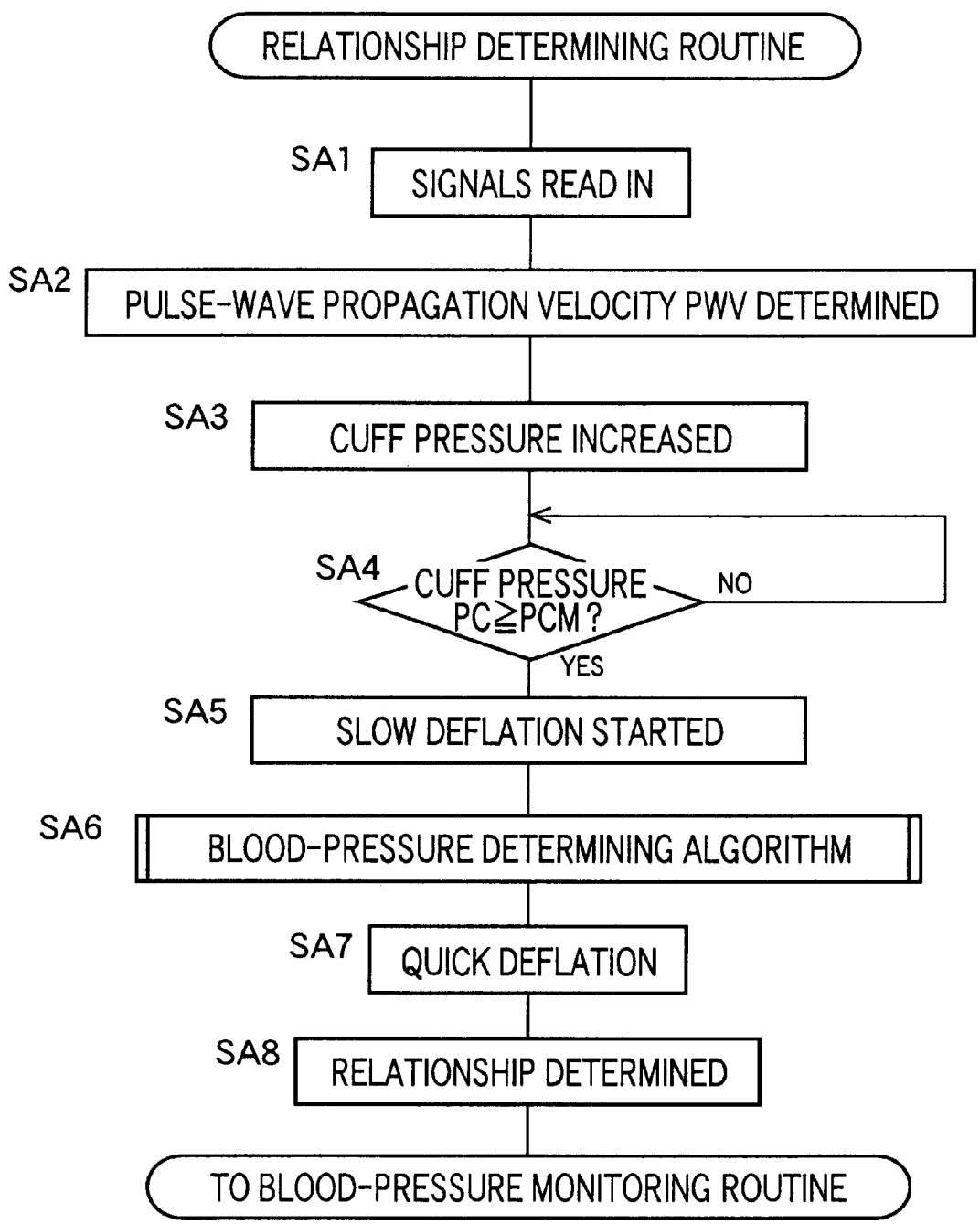
FIG. 6 is a flow chart representing a relationship determining routine according to which the control device shown in FIG. 1 determines a relationship between estimated blood pressure EBP and pulse-wave propagation velocity PWV.
Figure 7:
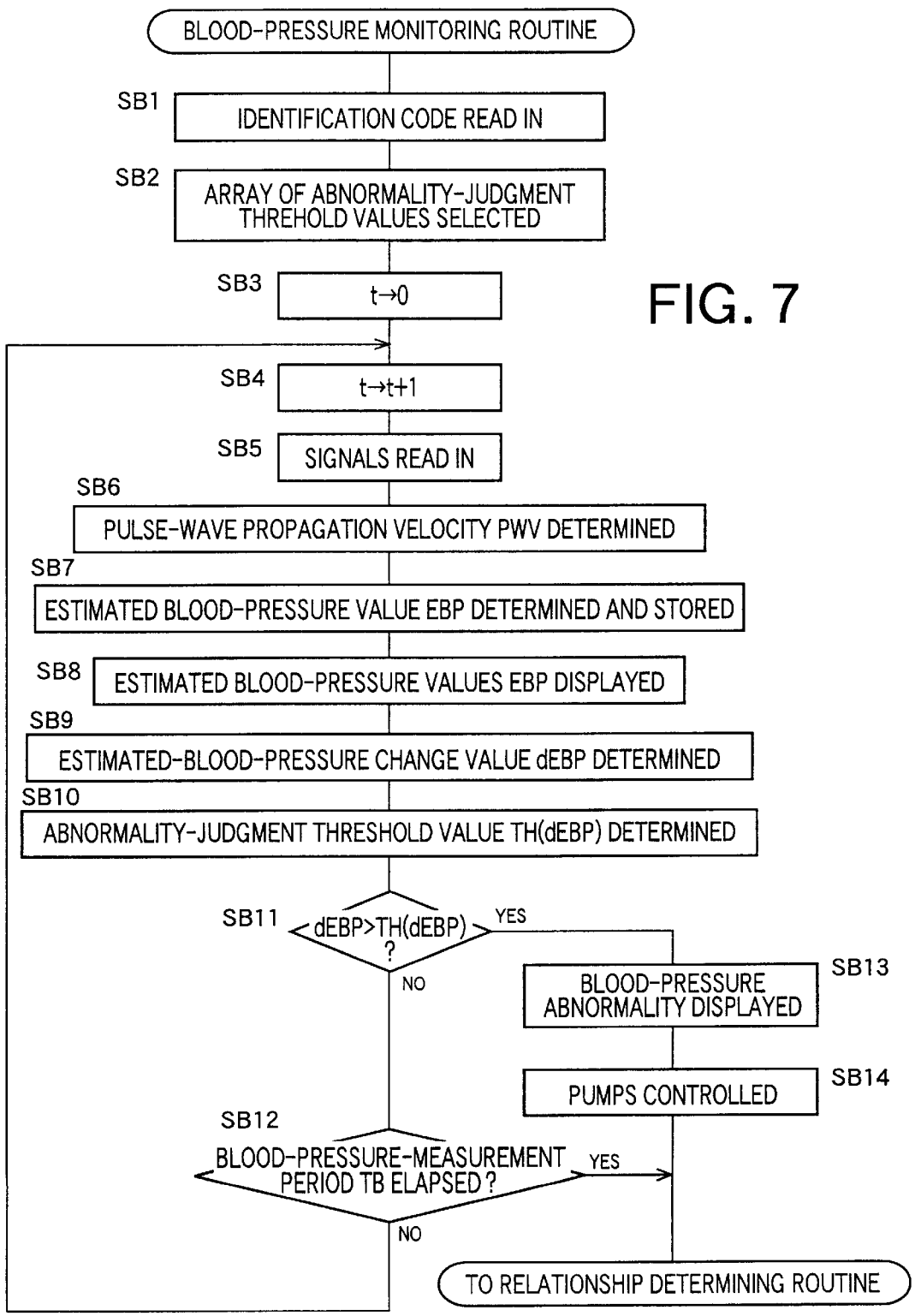
FIG. 7 is a flow chart representing a blood-pressure monitoring routine according to which the control device shown in FIG. 1 monitors blood pressure of a patient based on estimated blood-pressure values EBP.

FIGS. 6 and 7 are flow charts for explaining the essential control functions of the control device 28. FIG. 6 shows a relationship determining routine according to which the control device 28 determines a relationship between estimated blood pressure EBP and pulse-wave propagation velocity PWV; and FIG. 7 shows a blood-pressure monitoring routine according to which the control device 28 monitors blood pressure of a patient based on estimated blood-pressure values EBP.

First, the relationship determining routine of FIG. 6 will be described below. An initial control cycle according to this control routine is started at substantially the same time as the time when a dialysis operation is started. The operation of the dialysis section 8 is manually started by a doctor or a nurse.

In FIG. 6, at Step SA1 (hereinafter, "Step" is omitted, if appropriate), the control device 20 reads in one heartbeat-synchronous pulse of the ECG signal SE supplied from the electrocardiograph 42, and a corresponding heartbeat-synchronous pulse of the photoelectric-pulse-wave signal SM2 supplied from the photoelectric pulse-wave sensor 32.

Subsequently, the control goes to SA2 corresponding to the pulse-wave-propagation-velocity determining means 94. At SA2, the control device determines an R-wave of the ECG wave represented by the ECG signal SE read in at SA1, and a rising point of the photoelectric pulse wave represented by the photoelectric-pulse-wave signal SM2 read in at SA1, and additionally determines, as a pulse-wave propagation time DT, a time difference between the time of occurrence of the R-wave and the time of occurrence of the rising point, as illustrated in FIG. 4. In addition, the control device determines, according to the expression (1), a pulse-wave propagation velocity PWV based on the thus determined pulse-wave propagation time DT.

Subsequently, the control goes to SA3, SA4, and SA5 corresponding to the cuff-pressure changing means 90. At SA3, the control device switches the deflation control valve 16 to its pressure-supply position and starts the air pump 18, so that the pressure of the cuff 10 is increased. Then, at SA4, the control device judges whether the cuff pressure PC has reached the target pressure PCM. If a negative judgment is made at SA4, SA4 is repeated. Meanwhile, if a positive judgment is made at SA4, the control goes to SA5 to stop the air pump 18 and switch the deflation control valve 16 to its slow-deflation position, so that the pressure of the cuff 10 is slowly decreased at the prescribed rate, e.g., about 3 mmHg/sec.

Then, the control goes to SA6 corresponding to the blood-pressure determining means 92. At SA6, the control device determines, based on the change of respective amplitudes of respective heartbeat-synchronous pulses of the cuff pulse wave KW represented by the cuff-pulse-wave signal SM1 continuously obtained during the slow decreasing of the cuff pressure PC, a systolic, a mean, and a diastolic blood-pressure value $BP_{SYS}$, $BP_{MEAN}$, $BP_{DIA}$ of the patient, according to well-known oscillometric blood-pressure determining algorithm. In addition, the control device operates the display device 60 to display the thus determined blood-pressure values BP.

SA6 is followed by SA7 corresponding to the cuff-pressure changing means 90. At SA7, the control device switches the deflation control valve 16 to its quick-deflation position, so that the pressure in the cuff 10 is quickly decreased.

Next, the control goes to SA8 corresponding to the relationship determining means 96. At SA8, the control device determines the coefficients α, β of the expression (2) based on a first combination of the pulse-wave propagation velocity PWV determined at SA2 and the systolic blood-pressure value $BP_{SYS}$ determined at SA6, each in the current control cycle according to the present routine, and a second combination of a pulse-wave propagation velocity PWV determined at SA2 and a systolic blood-pressure value $BP_{SYS}$ determined at SA6, each in the preceding, i.e., last control cycle according to this routine. If the current control cycle is the initial or first control cycle according to this routine, the control device uses, as the above-indicated second combination, a combination of a standard pulse-wave propagation velocity PWV and a standard systolic blood-pressure value $BP_{SYS}$ pre-stored in the ROM 56. After the relationship is thus determined, the control device quits this routine and proceeds with the blood-pressure monitoring routine of FIG. 7.

Next, the blood-pressure monitoring routine of FIG. 7 will be described. First, the control device 28 carries out SB1 and SB2 corresponding to the selecting means 102. At SB1, the control device receives the ID code supplied from the ID-code reading device 50. Then, at SB2, the control device selects, based on the ID code received at SB1, an array of abnormality-judgment threshold values for the patient who is undergoing a dialysis operation, from the plurality of arrays of abnormality-judgment threshold values stored in the memory device 48. The following description will be made on the assumption that the array of abnormality-judgment threshold values for the patient "No. 1" shown in FIG. 5 are selected at SB2.

Subsequently, at SB3, the control device resets a timer, t, to zero (i.e., t=0) and, at SB4, the control device adds one to timer t. SB5 and SB6 are identical with SA1 and SA2, respectively. That is, at SB5, the control device reads in one heartbeat-synchronous pulse of the ECG signal SE and a corresponding heartbeat-synchronous pulse of the photoelectric-pulse-wave signal SM2 and, at SB6, the control device determines a pulse-wave propagation velocity PWV based on the thus read-in ECG signal SE and photoelectric-pulse-wave signal SM2.

Figure 8:
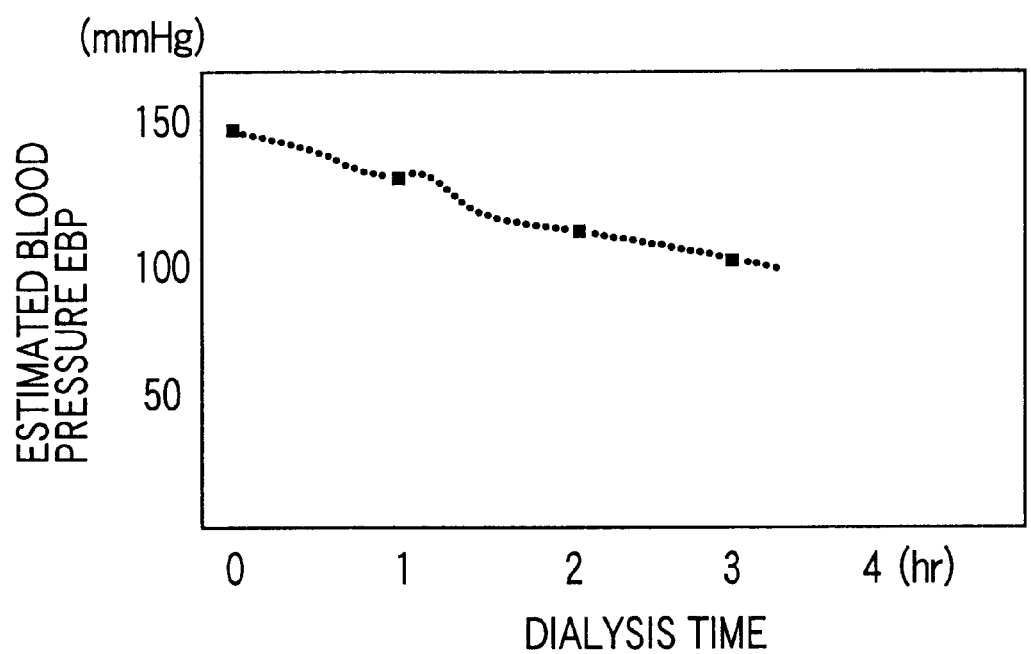
FIG. 8 is a graph showing an example of a timewise change of estimated blood-pressure values EBP, displayed at Step SB8 of FIG. 7.

Then, the control goes to SB7 and SB8 corresponding to the estimated-blood-pressure determining means 98. At SB7, the control device determines, according to the expression (2) whose coefficients have been determined at SA8 of FIG. 6, an estimated blood-pressure value EBP based on the pulse-wave propagation velocity PWV determined at SB6, and stores the thus determined, estimated blood-pressure value EBP in a prescribed area of the RAM 58. Then, at SB8, the control device operates the display device 60 to display a time-wise change of estimated blood-pressure values EBP including the current estimated blood-pressure value EBP determined at SB7, as shown in FIG. 8. In the graph shown in FIG. 8, black rectangular symbols "■", plotted at a regular interval of one hour, indicate blood-pressure values BP each determined according to the relationship determining routine of FIG. 6, i.e., measured using the cuff 10.

Then, the control goes to SB9 corresponding to the change-value determining means 100. At SB9, the control device determines an estimated-blood-pressure change rate dEBP (%), i.e., a rate of change of the estimated blood-pressure value EBP determined at SB7, from the systolic blood-pressure value $BP_{SYS}$ determined at SA6 of FIG. 6, according to the following expression (3):

$$dEBP=(|EBP-BP_{SYS}|/BP_{SYS})\times 100 \qquad \text{(Expression 3)}$$

Subsequently, the control goes to SB10 and SB11 corresponding to the blood-pressure-abnormality judging means 104. At SB10, the control device selects, from the array of abnormality-judgment threshold values selected at SB2, one abnormality-judgment threshold value TH(dEBP) corresponding to the current dialysis time indicated by the timer t. Regarding the patient "No. 1" shown in FIG. 5, the abnormality-judgment threshold value TH(dEBP) of 15% corresponds to one hour after the commencement of the dialysis operation, and the threshold value TH(dEBP) of 30% corresponds to the remaining time period of the dialysis operation. Then, at SB11, the control device judges whether the estimated-blood-pressure change rate dEBP determined at SB9 is greater than the abnormality-judgment threshold value TH(dEBP) selected at SB10.

If a negative judgment is made at SB11, the control goes to SB12 to judge whether the timer t indicates that the prescribed blood-pressure-measurement period TB equal to one hour has elapsed from the commencement of the current dialysis operation. If a negative judgment is made, SB4 and the following steps are repeated to monitor the blood pressure of the patient based on each estimated blood-pressure value EBP.

On the other hand, if a positive judgment is made at SB11, that is, if it is judged based on the estimated blood-pressure value EBP that the blood pressure of the patient is abnormal, the control goes to SB13 corresponding to the abnormality displaying means 106. At SB13, the control device operates the display device 60 to display an indication that the blood pressure of the patient is abnormal. SB13 is followed by SB14 corresponding to the fluid-amount control means 108. At SB14, the control device lowers the respective rotation speeds of the negative-pressure pump 66 and the blood-circulation pump 70 to respective prescribed rotation speeds. Then, the control proceeds with the relationship determining routine of FIG. 6 so as to carry out a blood-pressure measurement using the cuff 10. Meanwhile, if a positive judgment is made at SB12, that is, if the blood-pressure-measurement period TB has elapsed after the relationship determining routine of FIG. 6 has been last carried out, the control goes to the routine of FIG. 6.

As is apparent from the foregoing description of the illustrated embodiment in which the flow charts of FIGS. 6 and 7 are employed, at SB9 (i.e., the change-value determining means 100), the control device 28 determines the estimated-blood-pressure change rate dEBP representing the change of the estimated blood-pressure value EBP determined at SB7 (i.e., the estimated-blood-pressure determining means 98); and at SB10 and SB11 (i.e., the blood-pressure-abnormality judging means 104), the control device may judge, even if the estimated-blood-pressure change rate dEBP may be small, that the blood pressure of the patient is abnormal, during the initial one-hour period after the commencement of the dialysis operation during which the blood-pressure of the patient is highly likely to lower. In other words, even if the estimated-blood-pressure change rate dEBP may be great, the control device may not judge that the blood pressure of the patient is abnormal, during the remaining period of the dialysis operation during which the blood-pressure of the patient is not likely to lower. Thus, the control device can quickly judge or find an abnormal decrease of the blood pressure of the patient while not erroneously judging normal blood-pressure decreases as abnormal.

In addition, in the illustrated embodiment in which the flow charts of FIGS. 6 and 7 are employed, if the control device finds the abnormality of the blood pressure of the patient at SB10 and SB11 (i.e., the blood-pressure-abnormality judging means 104), then the control device automatically lowers the supply amount of the dialyzing fluid, so that the blood pressure of the patient may be quickly recovered.

Next, there will be described another embodiment of the present invention. In the following description, the same reference numerals as used in the preceding embodiment shown in FIGS. 1 to 8 are used to designate the corresponding elements or parts of the present embodiment, and the description thereof is omitted.

Figure 9:
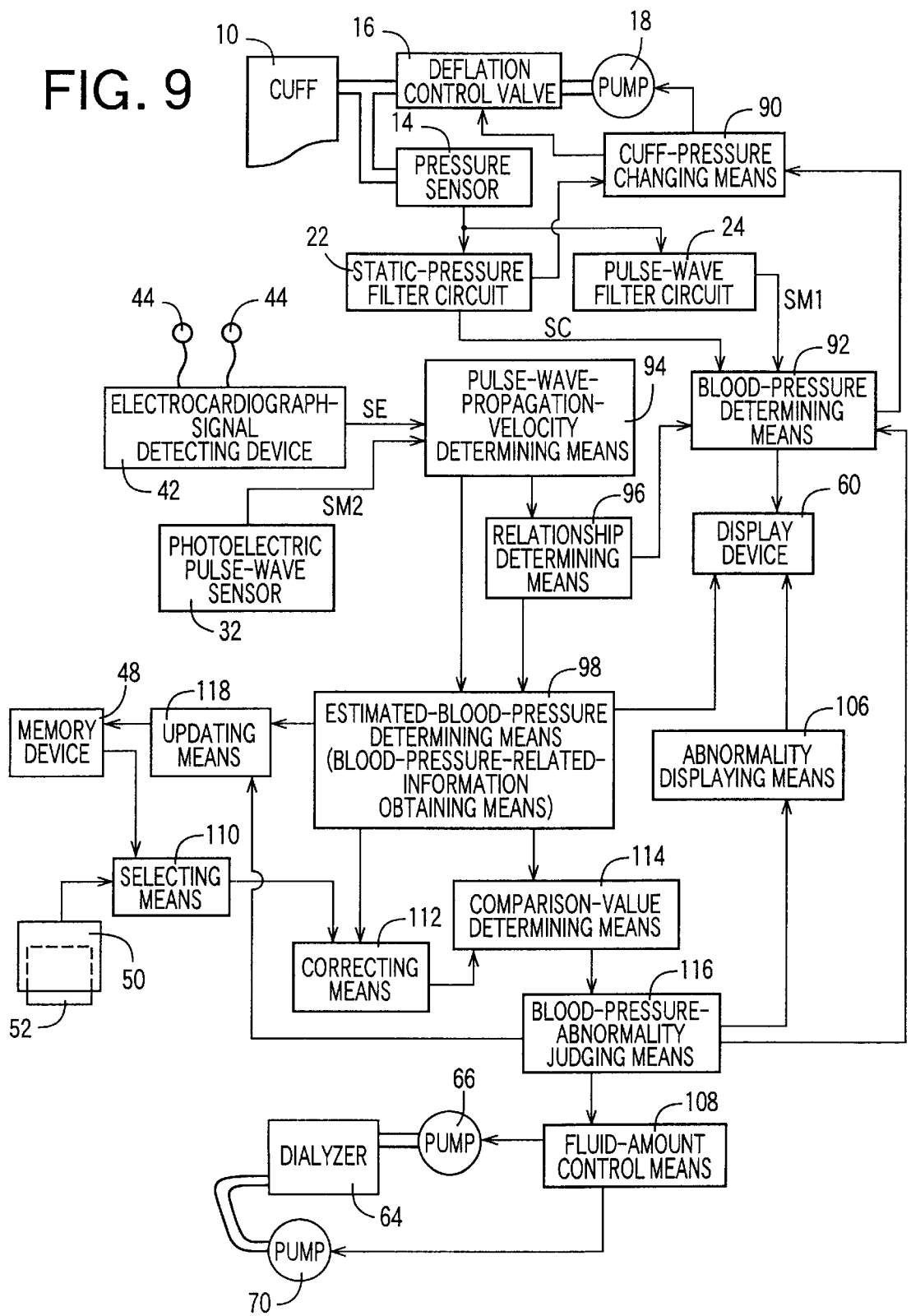
FIG. 9 is a block diagram corresponding to FIG. 3, for explaining essential control functions of a control device of another dialyzing apparatus as another embodiment of the present invention.

FIG. 9 shows a block diagram for explaining essential control functions of a control device 28 of another dialyzing apparatus as the second embodiment of the present invention. The second embodiment differs from the first embodiment only with respect to the control functions of the control device 28. However, a memory device 48 stores, in place of the arrays of abnormality-judgment threshold values, respective normal estimated-blood-pressure-and-dialysis-time relationships for respective individual patients. In addition, the control functions of the control device 28 employed in the second embodiment differs from those of the control device 28 employed in the first embodiment, only with respect to a selecting means 110, a correcting means 112, a comparison-value determining means 114, a blood-pressure-abnormality judging means 116, and an updating means 118. Hereinafter, those means will be described.

Figure 10:
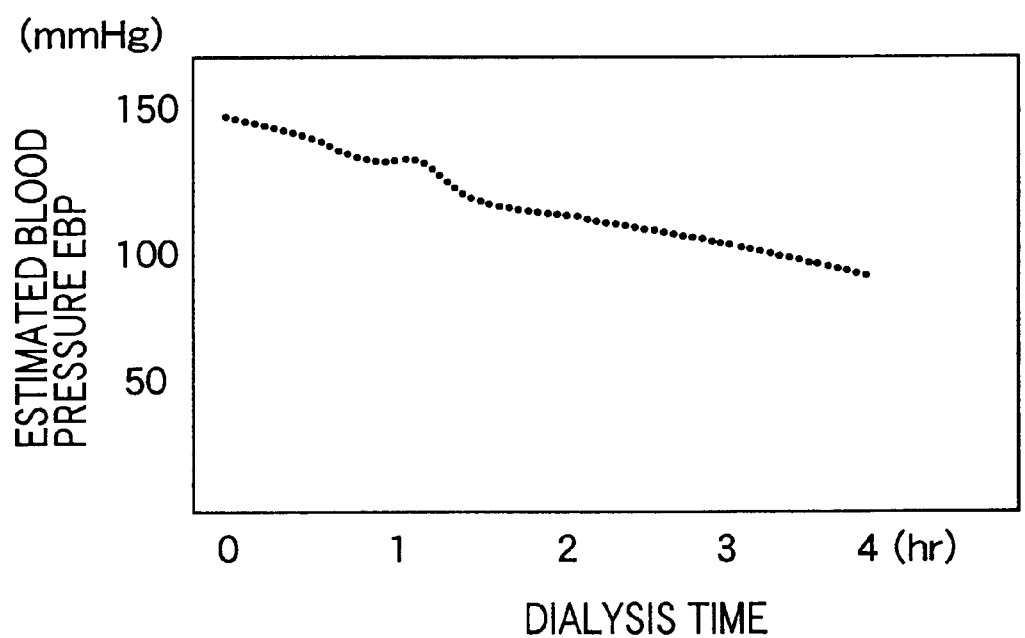
FIG. 10 is a graph showing an example of a normal relationship between estimated blood-pressure values and dialysis time, stored in a memory device shown in FIG. 9.

The selecting means 110 identifies, based on an ID code read by the ID-code reading device 50, a patient who is undergoing a dialysis treatment, and selects, from the normal estimated-blood-pressure-and-dialysis-time relationships stored in the memory device 48 for the individual patients, one normal relationship for the identified patient. A normal estimated-blood-pressure-and-dialysis-time relationship is a relationship between normal estimated blood-pressure values EBP and dialysis time, as shown in FIG. 10. The control device 28 collects, from each patient during a prescribed past time duration, respective estimated-blood-pressure-and-dialysis-time relationships in respective dialysis operations in which no blood-pressure abnormalities are found or judged, determines an average of the thus collected normal relationships, and stores, in the memory device 48, the thus determined average normal relationship for the patient. Since estimated blood pressure EBP is blood-pressure-related information that changes in relation with blood pressure of the patient, each normal estimated-blood-pressure-and-dialysis-time relationship is a sort of normal blood-pressure-related-information-and-dialysis-time relationship.

The correcting means 112 determines a difference (hereinafter, referred to as the "initial difference") between an estimated blood-pressure value EBP determined by the estimated-blood-pressure determining means 98 at the time of commencement of a dialysis operation and an estimated blood-pressure value EBP at the time of commencement of a dialysis operation, represented by the normal estimated-blood-pressure-and-dialysis-time relationship selected by the selecting means 110 for the particular patient. In addition, the correcting means 112 adds the thus determined initial difference to each of all the estimated blood-pressure values EBP in the entire dialysis operation, represented by the normal estimated-blood-pressure-and-dialysis-time relationship selected by the selecting means 110, and thereby determines a corrected normal estimated-blood-pressure-and-dialysis-time relationship between corrected estimated blood pressure and dialysis time. That is, the correcting means 112 translates the normal estimated-blood-pressure-and-dialysis-time relationship, as shown in FIG. 10, along an EBP axis so that the initial estimated blood-pressure value represented by the relationship is equal to the estimated blood-pressure value actually determined according to the expression (2). The thus translated normal relationship is the corrected normal relationship.

The comparison-value determining means 114 determines a comparison value by comparing a corrected normal estimated blood-pressure value, represented by the corrected normal estimated-blood-pressure-and-dialysis-time relationship determined by the correcting means 112, that corresponds to each current dialysis time, and a corresponding one of estimated blood-pressure values successively determined by the estimated-blood-pressure determining means 98. Here, a comparison value may be defined as a difference between a corrected normal estimated blood-pressure value and an estimated blood-pressure value actually determined by the determining means 98, or a ratio of one of the two sorts of estimated blood-pressure values to the other value.

The blood-pressure-abnormality judging means 116 judges that a decrease of the blood pressure of the patient is abnormal, when the comparison value determined by the comparison-value determining means 114 is greater than a prescribed abnormality-judgment threshold value. When the judging means 116 judges that the blood pressure of the patient is abnormal, the judging means 116 operates the blood-pressure determining means 92 to measure, using the cuff 10, reliable blood-pressure values BP of the patient.

The updating means 118 updates the normal estimated-blood-pressure-and-dialysis-time relationship stored in the memory device 48 for the particular patient, based on the current estimated-blood-pressure-and-dialysis-time relationship obtained during the current dialysis operation, if no blood-pressure abnormality has been found or judged by the blood-pressure-abnormality judging means 116 during the current dialysis operation. Since the normal relationship stored in the memory device 48 is the average of the past normal relationships obtained during the respective past dialysis operations performed on the patient, the updating means 118 determines a new average of those past normal relationships additionally including the current normal relationship as the last normal relationship, and thereby updates the average normal relationship stored in the memory device 48.

Figure 11:
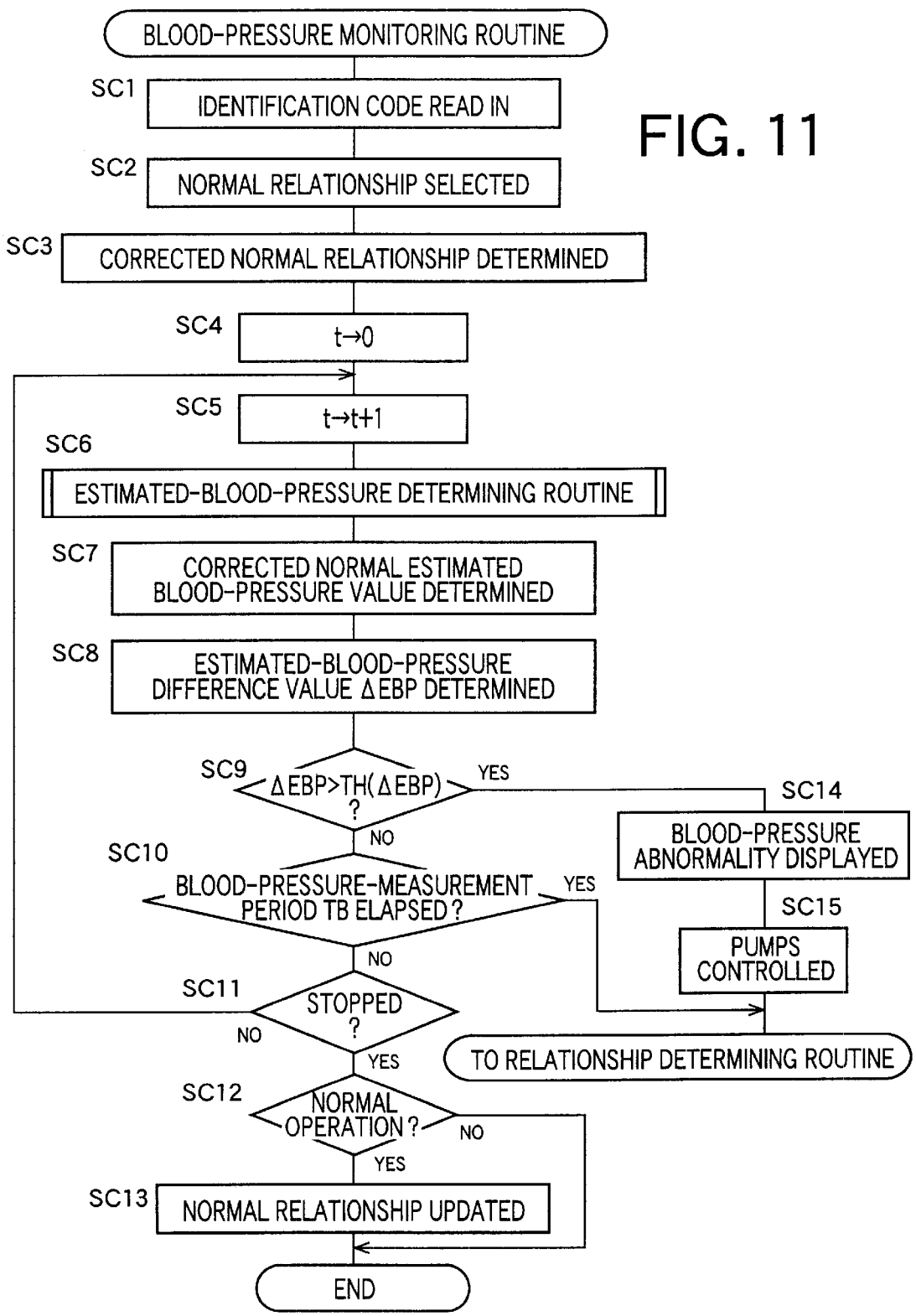
FIG. 11 is a flow chart corresponding to FIG. 7, representing a blood-pressure monitoring routine according to which the control device shown in FIG. 9 monitors blood pressure of a patient.

FIG. 11 is a flow chart for explaining the essential control functions of the control device 28, shown in FIG. 9. FIG. 11 shows a blood-pressure monitoring routine according to which the control device 28 monitors the blood pressure of a patient based on each estimated blood-pressure value EBP, after the control device 28 has determined a relationship between estimated blood pressure EBP and pulse-wave propagation velocity PWV according to the relationship determining routine of FIG. 6.

First, at SC1, the control device 28 receives the ID code read by the ID-code reading device 50. Then, at SC2, the control device selects, based on the ID code received at SC1, the normal estimated-blood-pressure-and-dialysis-time relationship for the patient who is undergoing a dialysis treatment or operation, from the normal estimated-blood-pressure-and-dialysis-time relationships stored in the memory device 48.

Subsequently, the control goes to SC3 corresponding to the correcting means 112. At SC3, the control device determines an initial difference, i.e., a difference between the estimated blood-pressure value EBP at the time of commencement of dialysis operation, represented by the normal estimated-blood-pressure-and-dialysis-time relationship selected at SC2, and the systolic blood-pressure value $BP_{SYS}$ determined according to the relationship determining routine of FIG. 6. In addition, the control device adds the thus determined, initial difference to each of all the estimated blood-pressure values EBP during the entire dialysis operation, represented by the normal relationship selected at SC2, and thereby determines a corrected normal estimated-blood-pressure-and-dialysis-time relationship.

Subsequently, at SC4, the control device resets timer t to zero (i.e., t=0) and, at SC5, the control device adds one to timer t. Then, the control goes to SC6, i.e., an estimated-blood-pressure determining routine corresponding to the pulse-wave-propagation-velocity determining means 94 and the estimated-blood-pressure determining means 98. This estimated-blood-pressure determining routine is identical with SB5, SB6, SB7, and SB8 of FIG. 7, that is, the control device determines a pulse-wave propagation velocity PWV based on the ECG signal SE and the photoelectric-pulse-wave signal SM2, determines an estimated blood-pressure value EBP based on the thus determined pulse-wave propagation velocity PWV and operates the display device 60 to display the thus determined, estimated blood-pressure value EBP.

Then, the control goes to SC7 and SC8 corresponding to the comparison-value determining means 114. First, at SC7, the control device determines a corrected normal estimated blood-pressure value, represented by the corrected normal relationship determined at SC3, that corresponds to a current dialysis time indicated by timer t. Then, at SC8, the control device determines, as a comparison value, a difference value ΔEBP between the estimated blood-pressure value EBP actually determined at SC6 and the corrected normal estimated blood-pressure value determined at SC7. The difference value ΔEBP is obtained as an absolute value.

Subsequently, the control proceeds with SC9 corresponding to the blood-pressure-abnormality judging means 116. At SC9, the control device judges whether the estimated-blood-pressure difference value ΔEBP determined at SC8 is greater than a prescribed abnormality-judgment threshold value TH(ΔEBP). A negative judgment made at SC9 indicates that the blood pressure of the patient undergoing the dialysis operation is normal.

If a negative judgment is made at SC9, then the control goes to SC10 to judge whether timer t indicates that the blood-pressure-measurement period TB equal to one hour has elapsed. If a negative judgment is made at SC10, the control goes to SC11 to judge whether a STOP switch, not shown, has been operated by an operator and a STOP signal has been supplied to the control device.

If a negative judgment is made at SC11, the control goes back to SC5 and the following steps so that the blood pressure of the patient is monitored based on each estimated blood-pressure value. On the other hand, if a positive judgment is made at SC11, the control goes to SC12 and SC13 corresponding to the updating means 118. First, at SC12, the control device judges whether the current dialysis operation has been finished normally. In other words, the control device judges whether any blood-pressure abnormalities have been judged during the current dialysis operation. If the control device judges that the dialysis operation has not been normal, then the control device quits this blood-pressure monitoring routine. On the other hand, if the control device judges that the dialysis operation has been normal, then the control goes to SC13 to update the normal estimated-blood-pressure-and-dialysis-time relationship stored in the memory device 48, based on the normal relationship obtained during the current dialysis operation.

On the other hand, if a positive judgment is made at SC9, the control goes to SC14 corresponding to the abnormality displaying means 106. At SC14, the control device operates the display device 60 to display an indication that the blood pressure of the patient is abnormal. SC14 is followed by SC15 corresponding to the fluid-amount control means 108. At SC15, the control device lowers the respective rotation speeds of the negative-pressure pump 66 and the blood-circulation pump 70 to respective prescribed low rotation speeds. Then, the control proceeds with the relationship determining routine of FIG. 6 so as to carry out a blood-pressure measurement using the cuff 10. Meanwhile, if a positive judgment is made at SC10, the control also goes to the routine of FIG. 6.

As is apparent from the foregoing description of the illustrated embodiment in which the flow charts of FIGS. 6 and 11 are employed, the memory device 48 stores, for a patient, a normal relationship between estimated blood pressure and dialysis time, and the normal relationship represents a normal change of blood pressure of the patient during a dialysis operation. At SC9 (i.e., the blood-pressure-abnormality judging means 116), the control device 28 judges a blood-pressure abnormality of the patient based on an estimated-blood-pressure difference value ΔEBP between each estimated blood pressure EBP determined at SC6 (i.e., the estimated-blood-pressure determining means 98) and a corresponding estimated blood pressure represented by the normal relationship.

That is, in the present embodiment, at SC9 (the blood-pressure-abnormality judging means 116), the control device finds the blood-pressure abnormality when the estimated-blood-pressure difference value ΔEBP determined at SC8 (i.e., the comparison-value determining means 114) is greater than the prescribed abnormality-judgment threshold value TH(ΔEBP). The estimated-blood-pressure difference value ΔEBP is the difference between the estimated blood-pressure value EBP actually determined at SC6 (the estimated-blood-pressure determining means 98) and the corrected normal estimated blood-pressure value, represented by the corrected normal relationship, that corresponds to the dialysis time. That is, at SC9 (the blood-pressure-abnormality judging means 116), the control device finds the blood-pressure abnormality of the patient by comparing the actually determined, estimated blood-pressure value EBP of the patient, with the corrected normal estimated blood-pressure value of the patient.

Thus, the control device 28 can find a blood-pressure abnormality of the patient based on only an abnormal change of the blood pressure of the patient, and accordingly can quickly find an abnormal decrease of the blood pressure of the subject while not erroneously judging normal blood-pressure decreases as abnormal.

In the present embodiment, at SC3 (i.e., the correcting means 112), the control device corrects the normal relationship stored in the memory device 48, to a corrected normal relationship, by adding a determined value to each of all the estimated blood-pressure values EBP represented by the normal relationship, such that the corrected estimated blood-pressure value, represented by the corrected normal relationship, at the time of commencement of the dialysis operation, is equal to the blood-pressure value BP actually determined at SC6. Therefore, the corrected estimated blood-pressure values represented by the corrected normal relationship do not contain any normal blood-pressure changes. And, at SC8 (i.e., the comparison-value determining means 114), the control device determines an estimated-blood-pressure difference value ΔEBP between each estimated blood-pressure value EBP actually determined and a corresponding corrected estimated blood-pressure value and, at SC9 (the blood-pressure-abnormality judging means 116), the control device finds or judges a blood-pressure abnormality based on the thus determined estimated-blood-pressure difference value ΔEBP. Therefore, in the present case, the control device can more quickly find an abnormal decrease of the blood pressure than in the case where the normal relationship stored in the memory device 48 is used as it is. In addition, the control device can less frequently judge normal blood-pressure decreases as abnormal.

In addition, in the present embodiment, at SC12 and SC13 (i.e., the updating means 118), the control device updates the normal relationship stored in the memory device 48, based on the current relationship between estimated blood pressure and dialysis time obtained during the current dialysis operation. Thus, the present apparatus can advantageously update the normal relationship for each patient, though the blood pressure of the patient naturally increases as his or her age increases. That is, the present apparatus can quickly find a blood-pressure abnormality of each patient though the blood pressure of the patient increases as his or her age increases, without erroneously judging normal blood-pressure decreases as abnormal.

Moreover, in the present embodiment, if the control device finds, at SC9 (the blood-pressure-abnormality judging means 116), the blood-pressure abnormality, then the control device automatically decreases, at SC15 (i.e., the fluid-amount control means 108), the amount of the dialyzing fluid supplied to the dialyzer 64. Therefore, the present apparatus can quickly recover the blood pressure of the patient.

Figure 12:
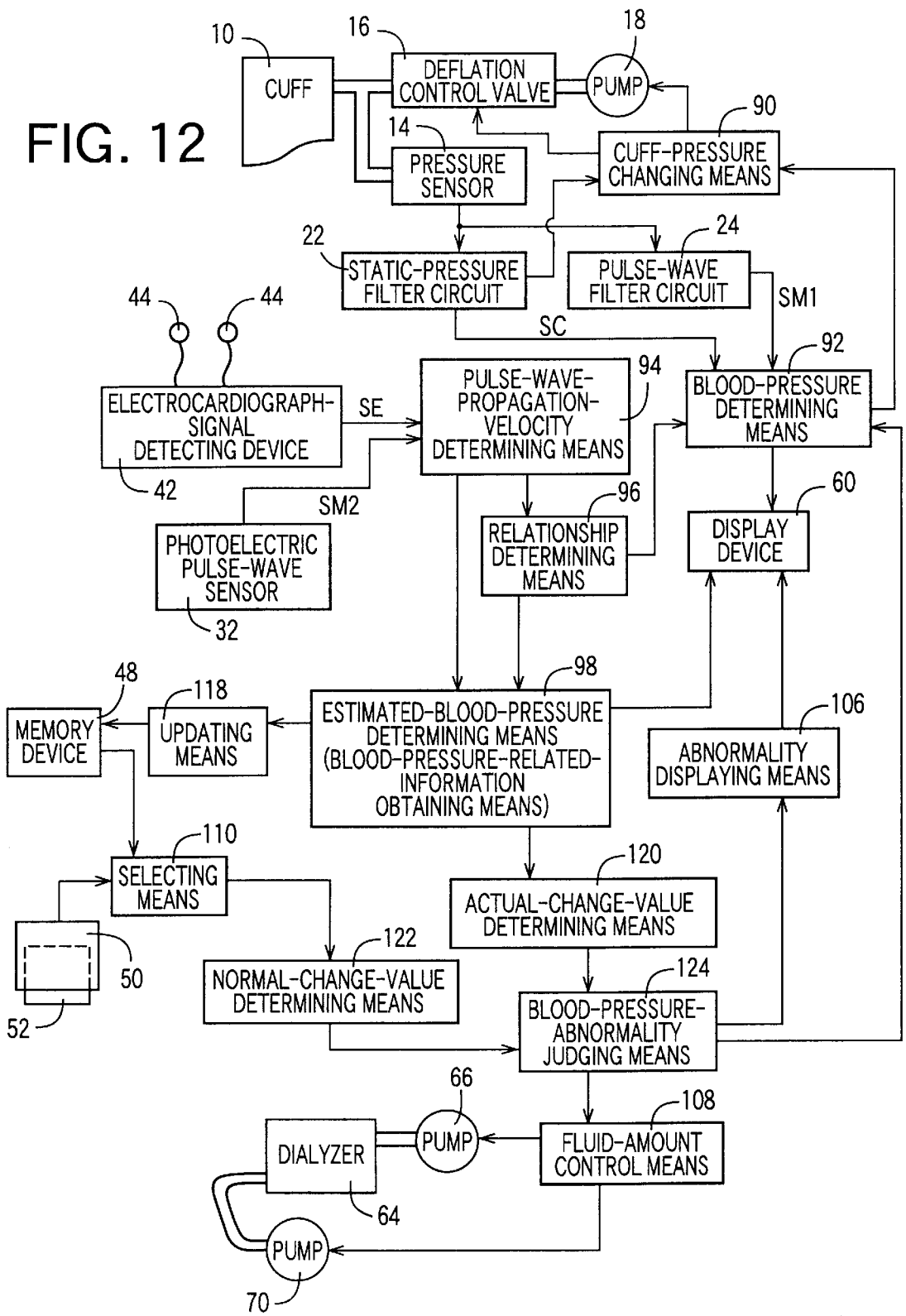
FIG. 12 is a block diagram corresponding to FIGS. 3 and 9, for explaining essential control functions of a control device of another dialyzing apparatus as yet another embodiment of the present invention.

Next, there will be described yet another embodiment of the present invention. FIG. 12 shows a block diagram for explaining essential control functions of a control device 28 of yet another dialyzing apparatus as the third embodiment of the present invention. The third embodiment differs from the first and second embodiments only with respect to the control functions of the control device 28. The control functions of the control device 28 employed in the third embodiment differs from those of the control device 28 employed in the second embodiment, only with respect to an actual-change-value determining means 120, a normal-change-value determining means 122, and a blood-pressure abnormality judging means 124. Hereinafter, those means will be described.

The actual-change-value determining means 120 successively determines an actual change value of each of the estimated blood-pressure values EBP successively determined by the estimated-blood-pressure determining means 98. Like in the first embodiment, the change value may be a rate of change or an amount of change. Thus, the actual change value is an actual rate of change, or an actual amount of change, of each of the estimated blood-pressure values EBP successively determined by the estimated-blood-pressure determining means 98, from a reference estimated blood-pressure value EBP. The reference estimated blood-pressure value EBP may be an estimated blood-pressure value EBP determined when the relationship is determined by the relationship determining means 96, i.e., a blood-pressure value BP determined by the blood-pressure determining means 92, or an estimated blood-pressure value EBP determined a prescribed time before the each estimated blood-pressure value EBP is determined.

The normal-change-value determining means 122 successively determines, based on the normal relationship between estimated blood pressure and dialysis time, selected for the identified patient by the selecting means 110, a normal change value of the estimated blood pressure during the same time period as the time period for which an actual change value is successively determined by the actual-change-value determining means 120. For example, in the case where the actual-change-value determining means 120 determines, as a reference estimated blood-pressure value EBP, an estimated blood-pressure value EBP that is equal to a blood-pressure value BP, measured using the cuff 10 two hours after the commencement of dialysis operation, to update the relationship between estimated blood pressure and pulse-wave propagation velocity, and determines an actual change value of an estimated blood-pressure value EBP determined fifteen minutes after, from the reference estimated blood-pressure value EBP, the normal-change-value determining means 122 determines, based on the normal relationship selected by the selecting means 110, a normal change value of the estimated blood pressure during a time period from two hours, to two hours and fifteen minutes, after the commencement of dialysis operation.

The blood-pressure-abnormality judging means 124 determines a difference between each of the actual change values successively determined by the actual-change-value determining means 120 and a corresponding one of the normal change values successively determined by the normal-change-value determining means 122 and, when the thus determined difference is greater than a prescribed threshold value, judges that the blood pressure of the patient has abnormally lowered. When this judgment is made, the judging means 124 operates the blood-pressure determining means 92 to start a blood-pressure measuring operation using the cuff 10 to obtain reliable blood-pressure values BP.

Figure 13:
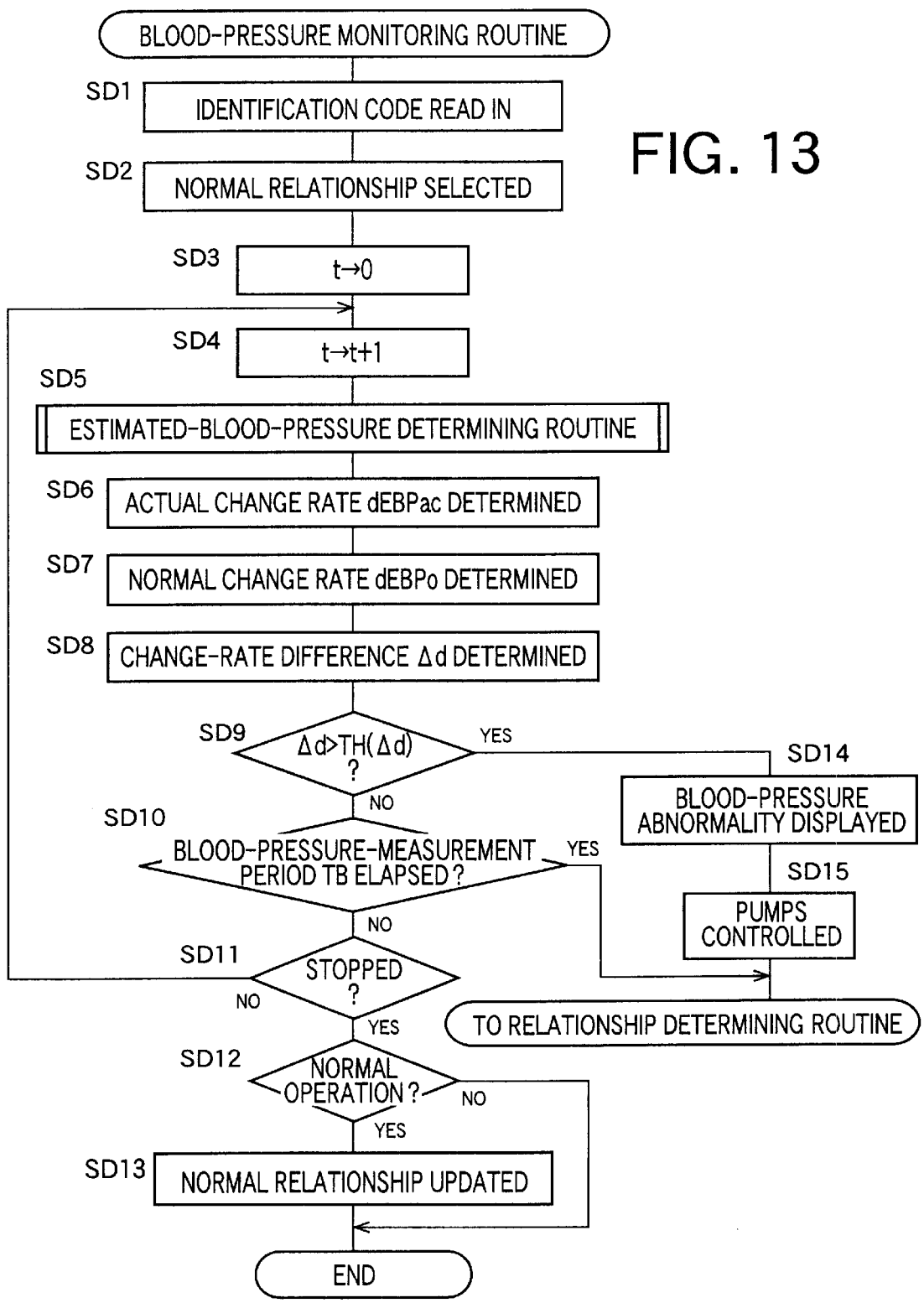
FIG. 13 is a flow chart corresponding to FIGS. 7 and 11, representing a blood-pressure monitoring routine according to which the control device shown in FIG. 12 monitors blood pressure of a patient.

FIG. 13 is a flow chart for explaining the essential control functions of the control device 28, shown in FIG. 12. FIG. 13 shows a blood-pressure monitoring routine according to which the control device 28 monitors the blood pressure of a patient based on each estimated blood-pressure value EBP, after the control device 28 has determined a relationship between estimated blood pressure EBP and pulse-wave propagation velocity PWV according to the relationship determining routine of FIG. 6.

SD1 and SD2 are identical with SC1 and SC2 of FIG. 11, and accordingly the control device selects the normal estimated-blood-pressure-and-dialysis-time relationship for the patient who is undergoing a dialysis treatment or operation, from the normal estimated-blood-pressure-and-dialysis-time relationships stored in the memory device 48. SD3, SD4, and SD5 are identical with SC4, SC5, and SC6 of FIG. 11 and accordingly the control device determines an estimated blood-pressure value EBP and operate the display device 60 to display the thus determined, estimated blood-pressure value EBP.

SD5 is followed by SD6 corresponding to the actual-change-value determining means 120. At SD6, the control device determines, as an actual change value, an actual rate of change, dEBPac (%), of the estimated blood-pressure value EBP determined at SD5, from the systolic blood-pressure value $BP_{SYS}$ determined in the last control cycle in accordance with the relationship determining routine of FIG. 6, according to the following expression (4):

$$dEBPac=(|EBP-BP_{SYS}|/BP_{SYS})\times 100 \qquad \text{(Expression 4)}$$

Then, the control goes to SD7 corresponding to the normal-change-value determining means 122. At SD7, the control device determines, as a normal change value, an actual rate of change, dEBPo (%), of estimated blood-pressure during a time period between a first time when the systolic blood-pressure value $BP_{SYS}$ is determined in the last control cycle in accordance with the relationship determining routine of FIG. 6, and a second time when the estimated blood-pressure value EBP is determined at SD5, according to the normal relationship between estimated blood pressure and dialysis time, selected at SD2. The determining means 122 determines the actual rate of change dEBPo according to an expression similar to the above-indicated expression (4).

Then, the control goes to SD8 and SD9 corresponding to the blood-pressure-abnormality judging means 124. First, at SD8, the control device determines a difference Δd between the actual change rate dEBPac determined at SD6 and the normal change rate dEBPo determined at SD7. The difference Δd is obtained as an absolute value. The change-rate difference Δd is a difference between the normal change of blood pressure of the patient who is undergoing the dialysis operation and the actual change of blood pressure of the patient.

Subsequently, at SD9, the control device judges whether the change-rate difference Δd determined at SD8 is greater than a prescribed threshold value TH(Δd), that is, whether the change of blood pressure of the patient during the current dialysis operation has excessively largely deviated from the normal change. If a negative judgment is made at SD9, the control goes to SD10 to SD13 that are identical with SC10 to SC13 of FIG. 11. On the other hand, if a positive judgment is made at SD9, the control goes to SD14 and SD15 that are identical with SC14 and SC15 of FIG. 11.

As is apparent from the foregoing description of the illustrated embodiment in which the flow charts of FIGS. 6 and 13 are employed, the memory device 48 stores, for a patient, a normal relationship between estimated blood pressure and dialysis time, and the normal relationship represents a normal change of blood pressure of the patient during a dialysis operation. At SD9 (i.e., the blood-pressure-abnormality judging means 124), the control device 28 judges a blood-pressure abnormality of the patient based on the difference value Δd between the normal change rate dEBPo determined from the normal relationship and the actual change rate dEBPac determined at SD6 (i.e., the actual-change-value determining means 120).

That is, in this embodiment, at SD8 and SD9 (the blood-pressure-abnormality judging means 124), the control device finds the blood-pressure abnormality when the difference between the normal change rate dEBPo and the actual change rate dEBPac is greater than the prescribed threshold value TH(Δd). Since the actual change rate dEBPac represents an actual change of blood pressure of the patient during a dialysis operation and the normal change rate dEBPo represents a normal change of blood pressure of the patient during the dialysis operation, the control device judges, at SD9 (the blood-pressure-abnormality judging means 124), a blood-pressure abnormality of the patient by comparing the actual blood-pressure change and the normal blood-pressure change with each other.

Thus, the control device can find a blood-pressure abnormality of the patient based on only an abnormal change of the blood pressure of the patient, and accordingly can quickly find an abnormal decrease of the blood pressure of the subject without erroneously judging normal blood-pressure decreases as abnormal.

While the present invention has been described in detail in its preferred embodiments, by reference to the drawings, the invention may otherwise be embodied.

For example, in each of the illustrated embodiments, each piece of blood-pressure-related information is obtained as each estimated blood-pressure value EBP, and the blood pressure of a patient during a dialysis operation is monitored based on the each estimated blood-pressure value EBP. However, the blood pressure of a patient during a dialysis operation may be monitored based on a different sort of blood-pressure-related information. For example, each pulse-wave propagation velocity PWV used to determine each estimated blood-pressure value EBP, or each pulse-wave propagation time DT corresponding, one to one, to the each velocity PWV may be used as each piece of blood-pressure-related information to monitor the blood pressure of a patient during a dialysis operation, since pulse-wave propagation velocity PWV or pulse-wave propagation time DT changes in relation with the blood pressure. In addition, since an area enveloped by each of successive heartbeat-synchronous pulses of the photoelectric pulse wave detected by the photoelectric-pulse-wave sensor 32 can be used as each piece of blood-pressure-related information, the blood pressure of a patient during a dialysis operation may be monitored based on the area enveloped by the each pulse of photoelectric pulse wave. Moreover, it is possible to employ a pressure-pulse-wave sensor which is adapted to be pressed against an artery, such as a radial artery, via skin and detects a pressure pulse wave produced from the artery. In the last case, each blood-pressure value that is determined, according to so-called "tonometry", based on the pressure pulse wave detected by the sensor may be used as each piece of blood-pressure-related information.

In addition, in each of the illustrated embodiments, the memory device 48 pre-stores, for individual patients, respective arrays of abnormality-judgment thresholds, or respective normal relationships between blood-pressure-related information and dialysis time, and the selecting means 102, 110 selects, for each patient who will undergo a dialysis treatment, a corresponding one array of abnormality-judgment thresholds, or a corresponding normal relationship between blood-pressure-related information and dialysis time. However, it is not essentially required that the memory device 48 should store respective arrays of abnormality-judgment thresholds, or respective normal relationships between blood-pressure-related information and dialysis time, for individual patients, or that the memory device 48 should store a plurality of arrays of abnormality-judgment thresholds, or a plurality of normal relationships between blood-pressure-related information and dialysis time. For example, the memory device 48 may be adapted to store a plurality of typical arrays of abnormality-judgment thresholds, or a plurality of typical normal relationships between blood-pressure-related information and dialysis time, and the control device 28 may be adapted to select one of the typical threshold arrays, or one of the typical normal relationships, that is the most appropriate for a particular patient who will undergo a dialysis treatment. Moreover, the magnetic card 52 carried by each patient may be used as a memory device which stores one array of abnormality-judgment thresholds, or one normal relationship between blood-pressure-related information and dialysis time, that is appropriate for the each patient. In the last case, the selecting means 102, 110 is omitted.

In the second embodiment shown in FIGS. 9, 10, and 11, the normal relationship between blood-pressure-related information and dialysis time, selected by the selecting means 110, is corrected by the correcting means 112 into the corrected normal relationship, and the comparison-value determining means 114 determines the comparison value according to the thus corrected normal relationship. However, the comparison-value determining means 114 may be adapted to determine a comparison value directly according to the normal relationship selected by the selecting means 110.

It is to be understood that the present invention may be embodied with other changes, improvements and modifications that may occur to a person skilled in the art without departing from the spirit and scope of the invention.

What is claimed is:

1. A blood-pressure monitoring apparatus for use with a dialyzing device, comprising:
    a blood-pressure-related-information obtaining device which iteratively obtains, from a patient who is undergoing a dialysis operation of the dialyzing device, a piece of blood-pressure-related information that can change in relation with a blood pressure of the patient;
    a change-value determining means for determining a change value representing a change of each piece of blood-pressure-related information iteratively obtained by the blood-pressure-related-information obtaining device;
    a memory device which stores, for the patient, a plurality of prescribed threshold values corresponding to a plurality of prescribed periods of an entire duration of the dialysis operation, wherein at least one of the threshold values that corresponds to at least one of the prescribed periods is smaller than the other threshold values, and wherein the blood pressure of the patient is more likely to lower during said at least one period of the entire duration, than during the other periods of the entire duration; and
    a judging means for judging that the blood pressure of the patient is abnormal, when the change value determined by the change-value determining means is greater than one of the threshold values that corresponds to one of the prescribed periods that includes a dialysis time, measured from a commencement of the dialysis operation, when said each piece of blood-pressure-related information is obtained by the blood-pressure-related-information obtaining device.

2. A dialyzing apparatus, comprising:
    a dialyzer;
    a pump which controls an amount of a dialyzing fluid that is supplied to the dialyzer;
    a blood-pressure monitoring apparatus according to claim 1; and
    a fluid-amount control means for controlling, when the judging means judges that the blood pressure of the patient is abnormal, the pump to decrease the amount of the dialyzing fluid supplied to the dialyzer.

3. An apparatus according to claim 1, wherein the blood-pressure-related-information obtaining device comprises a pulse-wave-propagation-velocity determining device which iteratively determines, as a piece of blood-pressure-related information, a pulse-wave propagation velocity at which a pulse wave propagates through an artery of the patient.

4. An apparatus according to claim 1, wherein the blood-pressure-related-information obtaining device comprises:
    a pulse-wave-propagation-velocity determining device which iteratively determines a pulse-wave propagation velocity at which a pulse wave propagates through an artery of the patient; and
    an estimated-blood-pressure determining means for iteratively determining, as a piece of blood-pressure-related information, an estimated blood pressure value of the patient based on each pulse wave propagation velocity iteratively determined by the pulse-wave-propagation-velocity determining device.

5. A blood-pressure monitoring apparatus for use with a dialyzing device, comprising:
    a blood-pressure-related-information obtaining device which iteratively obtains, from a patient who is undergoing a dialysis operation of the dialyzing device, a piece of blood-pressure-related information that can change in relation with a blood pressure of the patient;
    a memory device which stores a normal relationship between blood-pressure-related information and dialysis time; and
    a judging means for judging that the blood pressure of the patient is abnormal, when a comparison value is greater than a prescribed threshold value, the comparison value being obtained from each piece of blood-pressure-related information iteratively obtained by the blood-pressure-related-information obtaining device, with a piece of blood-pressure-related information, represented by the normal relationship stored in the memory device, that corresponds to a dialysis time, measured from a commencement of the dialysis operation, when said each piece of blood-pressure-related information is obtained by the blood-pressure-related-information obtaining device.

6. An apparatus according to claim 5, wherein the judging means comprises a comparison-value determining means for determining the comparison value by comparing said each piece of blood-pressure-related information obtained by the blood-pressure-related-information obtaining device, with the piece of blood-pressure-related information, represented by the normal relationship stored in the memory device, that corresponds to the dialysis time when said each piece of blood-pressure-related information is obtained by the blood-pressure-related-information obtaining device.

7. An apparatus according to claim 5, further comprising a correcting means for correcting an entirety of the normal relationship stored in the memory device, to a corrected normal relationship, such that a piece of blood-pressure-related information obtained by the blood-pressure-related-information obtaining device at a time of commencement of the dialysis operation is equal to a corrected piece of blood-pressure-related information, represented by the corrected normal relationship, that corresponds to the time of commencement of the dialysis operation, wherein the judging means comprises a comparison-value determining means for determining a comparison value by comparing a piece of blood-pressure-related information obtained by the blood-pressure-related-information obtaining device at a dialysis time measured from the time of commencement of the dialysis operation, with a corrected piece of blood-pressure-related information, represented by the corrected normal relationship, that corresponds to the dialysis time.

8. An apparatus according to claim 5, further comprising:
- an actual-change-value determining means for determining an actual change value of each piece of blood-pressure-related information iteratively obtained by the blood-pressure-related-information obtaining device; and
- a normal-change-value determining means for determining a normal change value by which the blood-pressure-related information, represented by the normal relationship stored in the memory device, changes in a period in which said each piece of blood-pressure-related information has changed by the actual change value determined by the actual-change-value determining means,
- wherein the judging means obtains the comparison value by comparing the actual change value determined by the actual-change-value determining means, with the normal change value determined by the normal-change-value determining means.

9. An apparatus according to claim 5, wherein the memory device stores, as the normal relationship, an average of a plurality of normal relationships, each between blood-pressure-related information and dialysis time, that have been obtained by the blood-pressure-related-information obtaining device during a plurality of dialysis operations which have been carried out on the patient, and wherein the apparatus further comprises an updating means for updating the normal relationship stored in the memory device, based on a relationship between blood-pressure-related information and dialysis time that is obtained by the blood-pressure-related-information obtaining device during the dialysis operation, when the judging means does not judge, during the dialysis operation, that the blood pressure of the patient is abnormal.

10. A dialyzing apparatus, comprising:
- a dialyzer;
- a pump which controls an amount of a dialyzing fluid that is supplied to the dialyzer;
- a blood-pressure monitoring apparatus according to claim 2; and
- a fluid-amount control means for controlling, when the judging means judges that the blood pressure of the patient is abnormal, the pump to decrease the amount of the dialyzing fluid supplied to the dialyzer.

* * * * *